United States Patent [19]

Abraham et al.

[11] Patent Number: 5,290,803

[45] Date of Patent: * Mar. 1, 1994

[54] USING ALLOSTERIC HEMOGLOBIN MODIFIERS TO DECREASE OXYGEN AFFINITY IN BLOOD

[75] Inventors: Donald J. Abraham, Midlothian, Va.; Mona Mahran, Alexandria, Egypt; Ahmed Mehanna, Winchester, Mass.; Ramnarayan Randad, Richmond, Va.

[73] Assignee: The Center of Innovative Technology, Herndon, Va.

[*] Notice: The portion of the term of this patent subsequent to Jun. 16, 2009 has been disclaimed.

[21] Appl. No.: 6,246

[22] Filed: Jan. 19, 1993

Related U.S. Application Data

[63] Continuation of Ser. No. 885,721, May 18, 1992, Pat. No. 5,248,785, which is a continuation-in-part of Ser. No. 702,947, May 20, 1991, Pat. No. 5,122,539, which is a continuation-in-part of Ser. No. 478,848, Feb. 12, 1990, Pat. No. 5,049,695.

[51] Int. Cl.$^5$ .................. A61K 31/40; A61K 31/325; C07C 45/00

[52] U.S. Cl. .................. 514/421; 514/512; 514/513; 514/533; 514/535; 514/538; 514/486; 514/833; 548/403; 548/478; 548/416; 548/473; 560/30; 560/31; 560/32; 568/452; 568/455

[58] Field of Search .............. 514/421, 512, 513, 533, 514/535, 538, 486, 833; 548/403, 478, 416, 473; 560/30, 31, 32; 568/452, 455

[56] References Cited

U.S. PATENT DOCUMENTS 5,122,539 6/1992 Abraham et al. .................. 514/563

Primary Examiner—Jose' G. Dees
Assistant Examiner—Porfirio Nazario-Gonzalez
Attorney, Agent, or Firm—Whitham & Marhoefer

[57] ABSTRACT

A family of compounds has been found to be useful for right-shifting hemoglobin towards a low oxygen affinity state. The compounds are capable of acting on hemoglobin in whole blood. In addition, the compounds can maintain the oxygen affinity in blood during storage and can restore the oxygen affinity of outdated blood.

8 Claims, 9 Drawing Sheets

USING ALLOSTERIC HEMOGLOBIN MODIFIERS TO DECREASE OXYGEN AFFINITY IN BLOOD

CROSS-REFERENCE TO RELATED APPLICATIONS

This patent application is a continuation application of the co-pending U.S. Pat. application entitled "USING ALLOSTERIC HEMOGLOBIN MODIFIERS TO DECREASE OXYGEN AFFINITY IN BLOOD" having U.S. Ser. No. 07/885,721, which was filed May 18, 1992, and which issued as U.S. Pat. No.5,248,785. That patent application was itself a continuation-in-part (CIP) having U.S. Ser. No. 07/702,947 now U.S. Pat. No. 5,122,539 which was filed May 20, 1991. That patent application was itself a continuation-in-part application having U.S. Ser. No. 07/478,848, now U.S. Pat. No. 5,049,695 which was filed on Feb. 12, 1990. The subject matter of this application is also a continuation-in-part of the copending U.S. Patent Application entitled "ALLOSTERIC HEMOGLOBIN MODIFIER COMPOUNDS" having U.S. Ser. No. 07/722,382 which was filed Jun. 26, 1991, and which itself is a continuation of the U.S. patent application Ser. No. 07/623,346 which was filed Dec. 7, 1990. The text of all three of the above-identified patent applications and U.S. Patent is herein incorporated by reference.

BACKGROUND OF THE INVENTION

1. Field of the Invention

The present invention generally relates to using a family of compounds to adjust the allosteric equilibrium of hemoglobin toward a low oxygen affinity state. Moreover, the invention contemplates using the family of compounds for use in treating diseases involving oxygen deficiency, in wound healing, and in restoring oxygen affinity of stored blood.

2. Description of the Prior Art

Hemoglobin is a tetrameric protein which delivers oxygen via an allosteric mechanism. Oxygen binds to the four hemes of the hemoglobin molecule. Each heme contains porphyrin and iron in the ferrous state. The ferrous iron-oxygen bond is readily reversible. Binding of the first oxygen to a heme requires much greater energy than the second oxygen molecule, binding the third oxygen requires even less energy, and the fourth oxygen requires the lowest energy for binding. Hemoglobin has two $\alpha$ and two $\beta$ subunits arranged with a two fold symmetry. The $\alpha$ and $\beta$ dimers rotate during oxygen release to open a large central water cavity. The allosteric transition that involves the movement of the alpha-beta dimer takes place between the binding of the third and fourth oxygen. The $\alpha_1\beta_1$ interface binding is tighter than the $\alpha_1\alpha_2$ or $\alpha_1\beta_2$ interfaces.

In blood, hemoglobin is in equilibrium between two allosteric structures. In the "T" (for tense) state, hemoglobin is deoxygenated. In the "R" (for relaxed) state, hemoglobin is oxygenated. An oxygen equilibrium curve can be scanned, using well known equipment such as the AMINCO ™ HEM-O-SCAN, to observe the affinity and degree of cooperativity (allosteric action) of hemoglobin. In the scan, the Y-axis plots the percent of hemoglobin oxygenation and the X-axis plots the partial pressure of oxygen in millimeters of mercury (mm Hg). If a horizontal line is drawn from the 50% oxygen saturation point to the scanned curve and a vertical line is drawn from the intersection point of the horizontal line with the curve to the partial pressure X-axis, a value commonly known as the $P_{50}$ is determined (i.e., this is the pressure in mm Hg when the scanned hemoglobin sample is 50% saturated with oxygen). Under physiological conditions (i.e., 37° C., pH=7.4, and partial carbon dioxide pressure of 40 mm Hg), the $P_{50}$ value for normal adult hemoglobin (HbA) is around 26.5 mm Hg. If a lower than normal $P_{50}$ value is obtained for the hemoglobin under test, the scanned curve is considered to be "left-shifted" and the presence of high affinity hemoglobin is indicated. Conv<xsely, if a higher than normal $P_{50}$ value is obtained for the hemoglobin under test, the scanned curve is considered to be "right-shifted" and the presence of low affinity hemoglobin is indicated.

It has been proposed that influencing the allosteric equilibrium of hemoglobin is a viable avenue of attack for treating diseases. The conversion of hemoglobin to a high affinity state is generally regarded to be beneficial in resolving problems with deoxy Hemoglobin-S (sickle cell anemia). The conversion of hemoglobin to a low affinity state is believed to have general utility in a variety of disease states where tissues suffer from low oxygen tension, such as ischemia and radio sensitization of tumors. Several synthetic compounds have been identified which have utility in the allosteric regulation of hemoglobin and other proteins. For example, several new compounds and methods for treating sickle cell anemia which involve the allosteric regulation of hemoglobin are reported in U.S. Pat. No. 4,699,926 to Abraham et al., U.S. Pat. No. 4,731,381 to Abraham et al., U.S. Pat. No. 4,731,473 to Abraham et al., U.S. Pat. No. 4,751,244 to Abraham et al., and U.S. Pat. No. 4,887,995 to Abraham et al. Furthermore, in both Perutz, "Mechanisms of Cooperativity and Allosteric Regulation in Proteins", Quarterly Reviews of Biophysics 22, 2 (1989), pp. 163-164, and Lalezari et al., "LR16, a compound with potent effects on the oxygen affinity of hemoglobin, on blood cholesterol, and on low density lipoprotein", Proc. Natl. Acad. Sci., USA 85 (1988), pp. 6117-6121, compounds which are effective allosteric hemoglobin modifiers are discussed. In addition, Perutz et al. has shown that a known antihyperlipoproteinemia drug, bezafibrate, is capable of lowering the affinity of hemoglobin for oxygen (see, "Bezafibrate lowers oxygen affinity of hemoglobin", Lancet 1983, 881.

German Patent Applications 2,149,070 and 2,432,560, both to Witte et al., disclose compounds which are structurally similar to some of the compounds in the family of compounds defined by this invention. However, the Witte et al. patent applications contemplate use of the compounds for the reduction of serum lipid levels. The Witte et al. patent applications do not provide any indication of the potential use of the compounds for allosteric hemoglobin modification.

SUMMARY OF THE INVENTION

It is therefore an object of the present invention to provide a method of using a family of compounds to allosterically modify hemoglobin such that the hemoglobin is present in blood in a lower oxygen affinity state.

It is another object of the present invention to provide a method of prolonging the storage life of blood by adding compounds within a particular family of compounds to the blood.

According to the invention, an allosteric hemoglobin modifying family of compounds is defined by the formula:

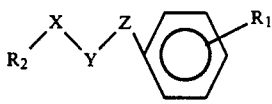

where $R_2$ is a substituted or unsubstituted aromatic such as a phenyl, naphthyl, or indanyl, or a heterocyclic aromatic, or a substituted or unsubstituted alkyl ring compound such as a cyclohexyl or adamantyl, or a substituted or unsubstituted phthalimide compound where X is a carboxyl, Y is a nitrogen and $R_2$ completes the phthalimide compound by being bonded to both X and Y, and where X, Y, and Z are $CH_2$, NH, CO, O or N with the caveat that the X, Y, and Z moieties are each different from one another, and where $R_1$ has the formula:

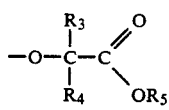

where R1 can be connected to any position on the phenyl ring and $R_3$ and $R_4$ are hydrogen, halogen, methyl, or ethyl groups and these moieties may be the same or different, or alkyl moieties as part of an aliphatic ring connecting $R_3$ and $R_4$, and $R_5$ is a hydrogen, loweralkyl such as methyl, ethyl or propyl, or a salt cation such as sodium, potassium, or ammonium. Many compounds within this family have been synthesized and their effect on the $P_{50}$ value of hemoglobin has been determined. Each of the compounds tested was found to increase the $P_{50}$ value of hemoglobin; hence, the compounds are capable of driving the allosteric equilibrium of hemoglobin towards a condition favoring the low oxygen affinity state. In addition, the compounds were found to stabilize the degree of oxygen dissociation of hemoglobin in stored blood over extended periods of time. Furthermore, the compounds were found to be well tolerated by mice when administered as an intraperitoneal dose. Because the compounds within the family defined by this invention are capable of shifting the hemoglobin allosteric equilibrium toward the low affinity "T" state, they have the ability to cause hemoglobin to deliver more oxygen to tissues. Thus, the compounds of the invention should be valuable as antiischemic agents, as sensitizers for x-ray irradiation in cancer therapy, as wound healing agents, in treating disorders related to low oxygen delivery in the brain such as Alzheimer's, depression, and schizophrenia, in preparing blood substitutes, and in blood storage.

BRIEF DESCRIPTION OF THE DRAWINGS

The foregoing and other objects, aspects and advantages will be better understood from the following detailed description of a preferred embodiment of the invention with reference to the drawings, in which:

FIGS. 1b and 1c are chemical structures defining two subsets of the family defined in FIG. 1a;

DETAILED DESCRIPTION OF THE PREFERRED EMBODIMENTS OF THE INVENTION

Figure 1A:
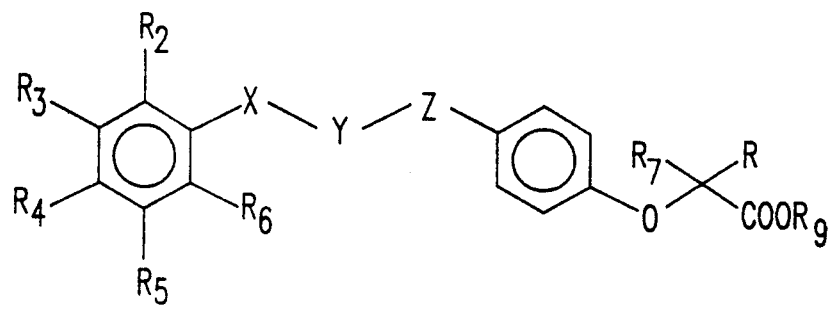
FIG. 1a is a chemical structure defining a particularly preferred group within the family of compounds used in the present invention.
Figure 1B:
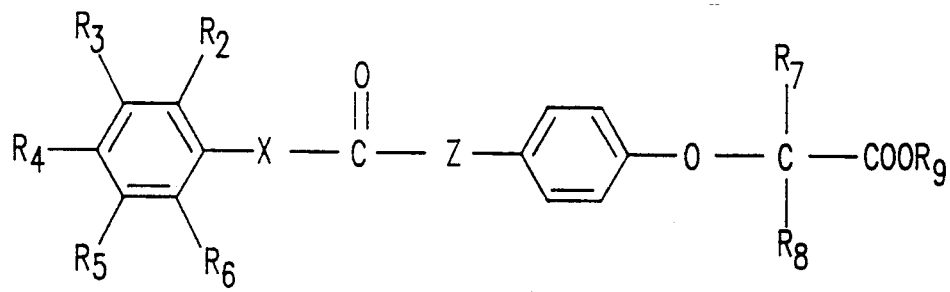
Figure 1C:
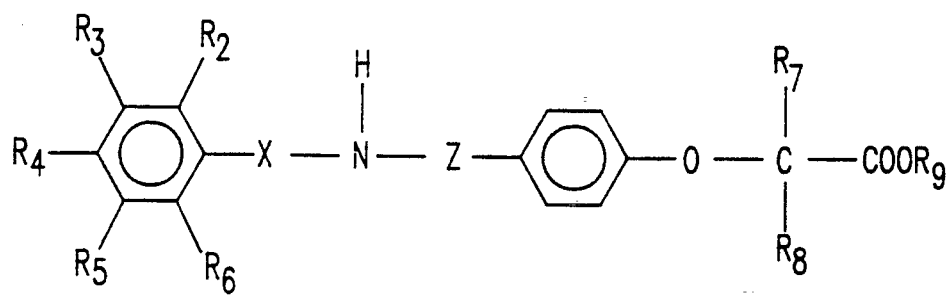

Referring now to the drawings and, more particularly, to FIGS. 1a-c which illustrate the general structural formula of particularly preferred compounds contemplated for use in the present invention and first and second subsets of the general structural formula, respectively. With reference to the general structural formula of FIG. 1a, the X and Z moieties may be $CH_2$, CO, NH or O, and the Y moiety may be CO or NH, with the caveat that the X, Y, and Z moieties are each different from one another. In addition, $R_{2-6}$ are either hydrogen, halogen, a substituted or unsubstituted $C_{1-3}$ alkyl group (up to three carbons in length), or a $C_{1-3}$ ester or ether and these moieties may be the same or different, or alkyl moieties of aliphatic or aromatic rings incorporating two adjacent $R_{2-6}$ sites. The $R_{7-8}$ positions are hydrogen, halogen, methyl, or ethyl groups and these moieties may be the same or diff<xent, or alkyl moieties as part of an aliphatic (e.g., cyclobutyl) ring connecting $R_7$ and $R_9$. The $R_9$ position is a hydrogen, halogen, $C_{1-3}$ loweralkyl such as methyl, ethyl or propyl, or a salt cation such as sodium, potassium, or ammonium.

Figure 2A:
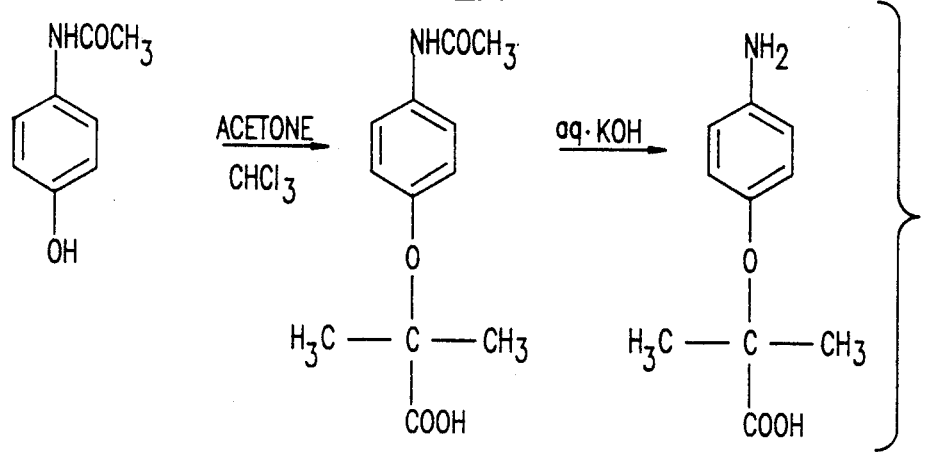
FIGS. 2a-b depict chemical structures of precursor compounds arranged in reaction schemes for preparing compounds that are useful as intermediates for synthesizing compounds within a first group of the family of compounds.
Figure 2B:
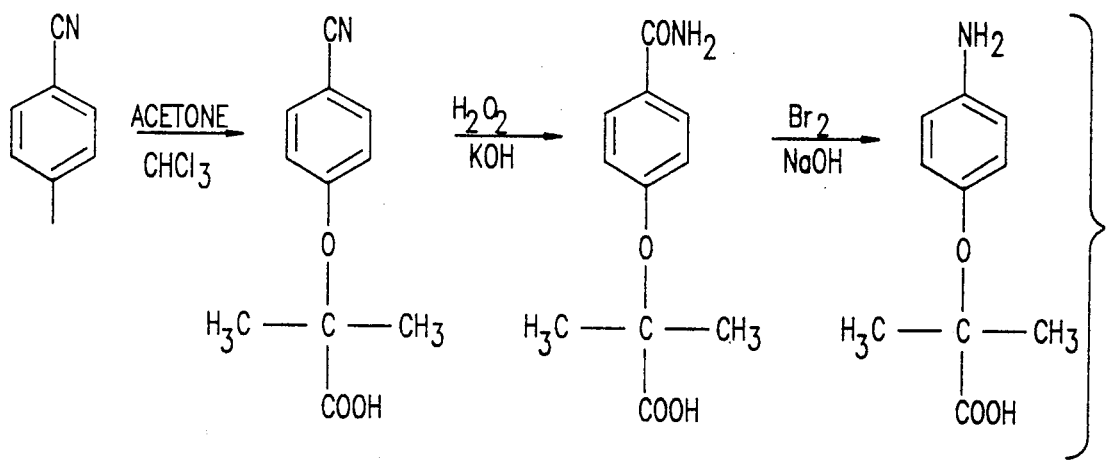
Figure 2C:
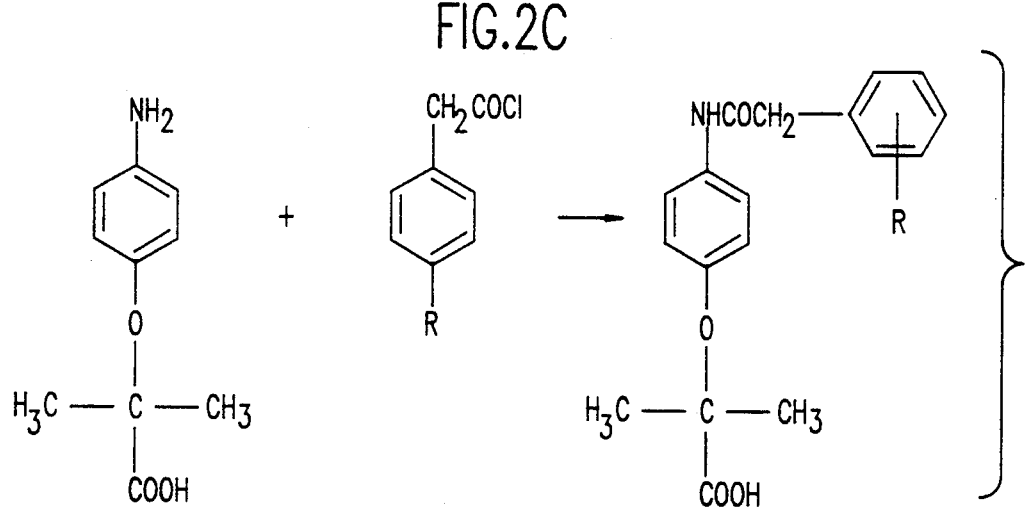
FIG. 2c depicts chemical structures, including the intermediates produced as shown in FIGS. 2a-b, arranged in a reaction scheme to prepare the first group of preferred compounds.
Figure 3:
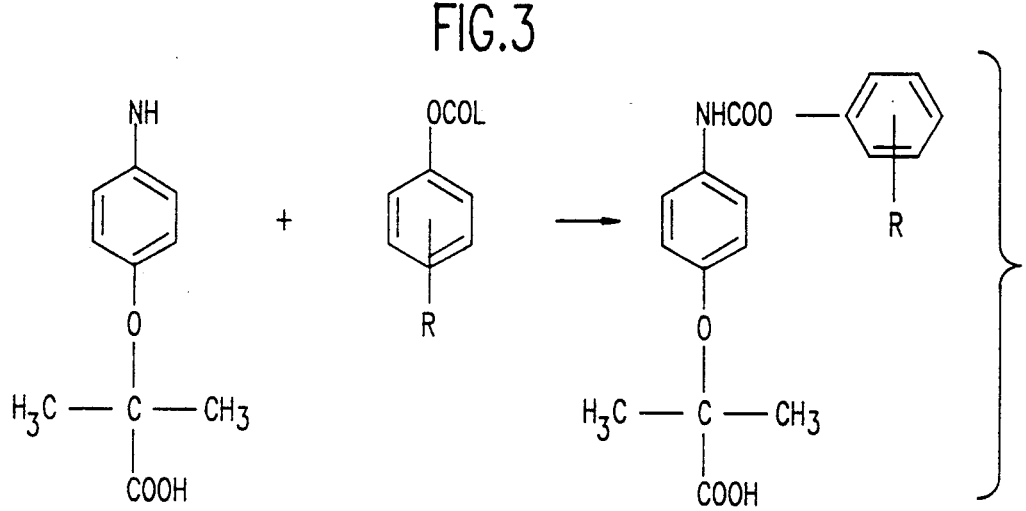
FIG. 3 depicts chemical structures arranged in a reaction scheme to produce a second group of the family of preferred compounds.
Figure 4:
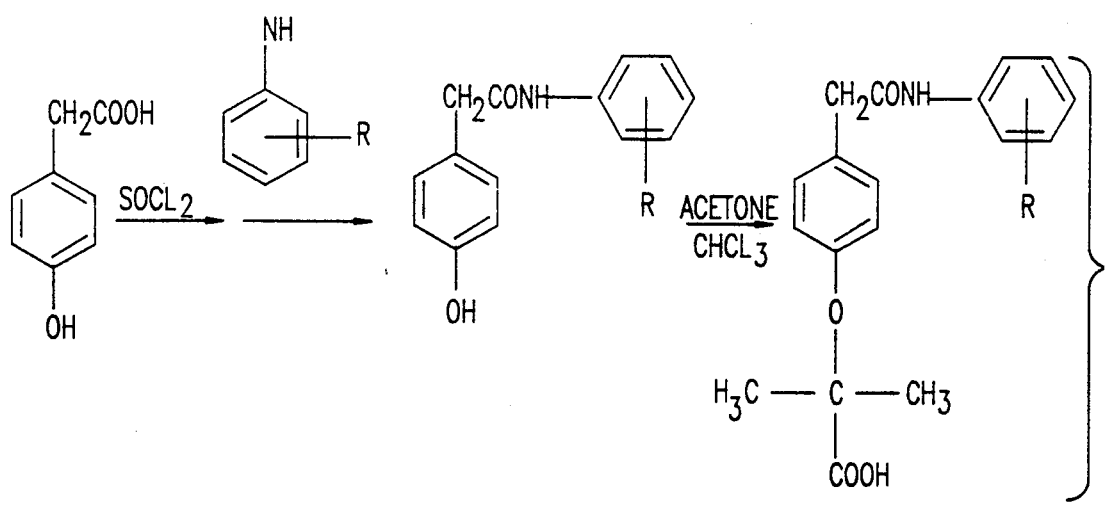
FIG. 4 depicts chemical structures arranged in a reaction scheme to produce a third group of the family of preferred compounds.
Figure 5A:
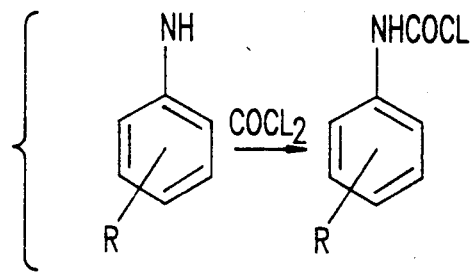
FIG. 5a-b depict chemical structures of precursor compounds arranged in reaction schemes for preparing compounds that are useful as intermediates for synthesizing compounds within a fourth group of the family of preferred compounds.
Figure 5B:
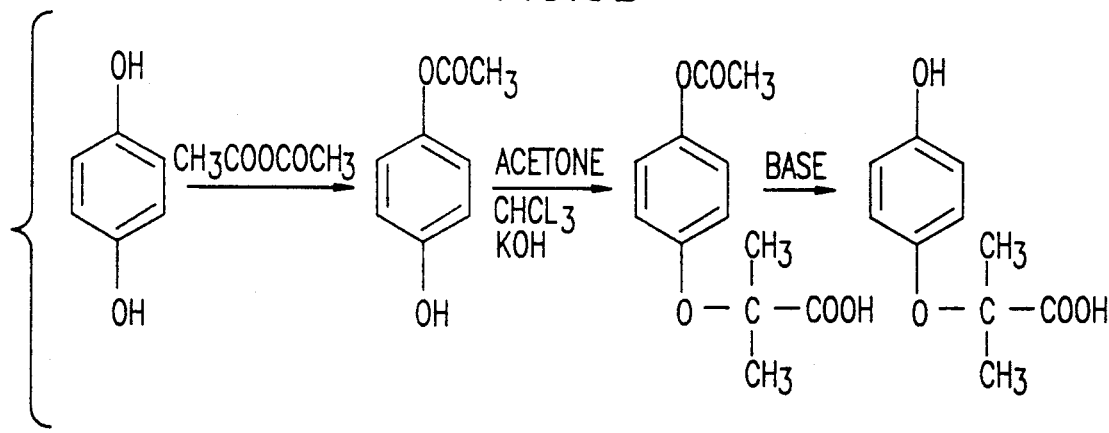
Figure 5C:
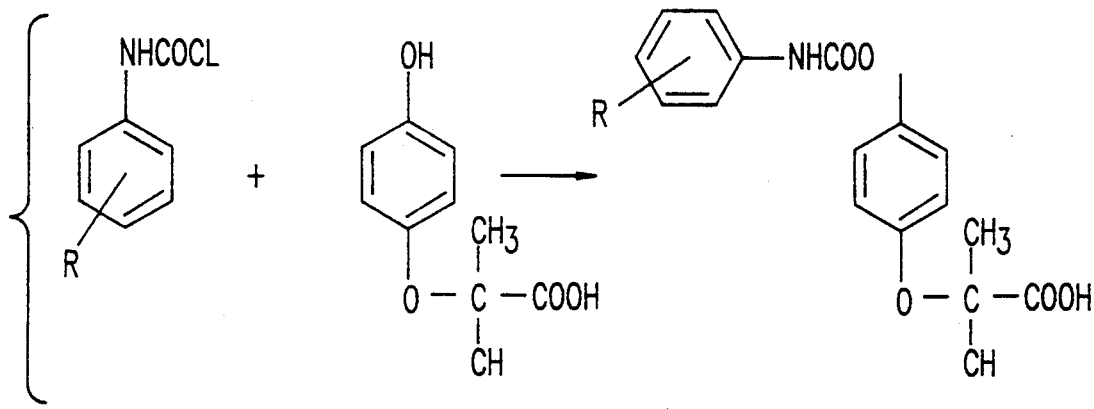
FIG. 5c depicts chemical structures, including the intermediates produced in FIGS. 5a-b, arranged in a reaction scheme to produce the fourth group of compounds.
Figure 6A:
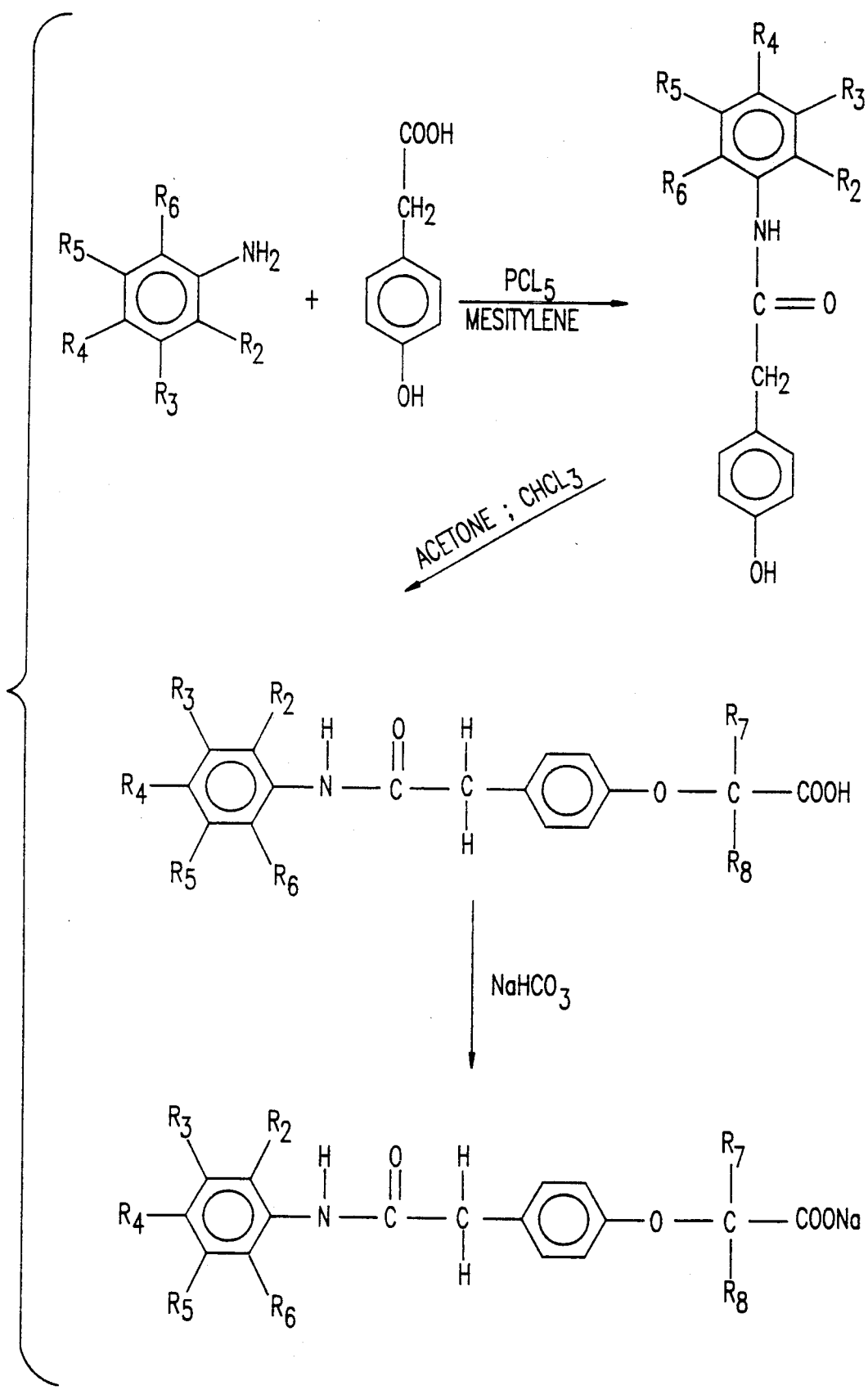
FIG. 6a depicts chemical structures arranged in a reaction scheme, which is an alternative to that shown in FIG. 4, for producing compounds within a third group of the family of preferred compounds.

In the first subset of compounds defined in FIG. 1b, X and Z may each be $CH_2$, NH, or O, with the caveat that when X is CH', Z is either NH or O, when X is NH, Z is either CH, or O, and when X is O, Z is NH or $CH_2$. The first subset of compounds may conveniently be classified into four groupings as follows:

Group I: 2-[4-((aryl)acetamido)phenoxy]-2-methyl propionic acid compounds having the general structural formula illustrated in FIG. 2C;

Group II: 2-[4-(((aryl)oxy)carbonyl)amino) phenoxy]-2-methyl propionic acid compounds having the general structural formula illustrated in FIG. 3;

Group III: 2-[4-((((aryl)amino)carbonyl) methyl)-phenoxy]-2-methyl propionic acid compounds having the general structural formula illustrated in FIGS. 4 and 6a; and Group IV: 2-[4-(((aryl)amino)carbonyl) oxy)phenoxy]-2-methyl propionic acid compounds having the general structural formula illustrated in FIG. 5C.

Figure 7A:
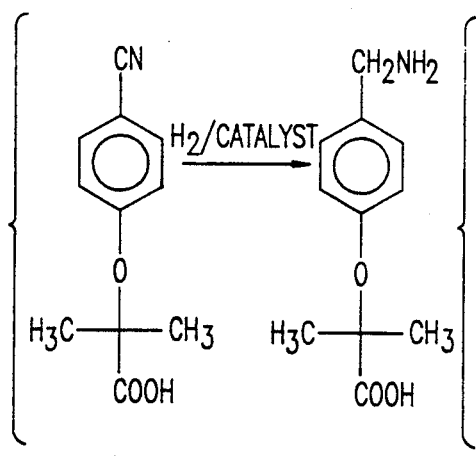
FIGS. 7a and 7b depict chemical structures arranged in a reaction scheme for producing compounds within a fifth group of the family of preferred compounds.
Figure 7B:
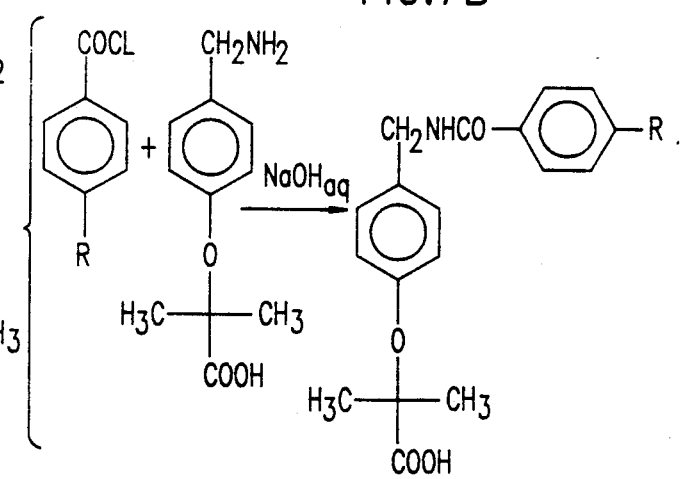

In the second subset of compounds defined in FIG. 1c, X and Z may each be CO or $CH_2$, with the caveat that when X is CO, Z is $CH_2$, and when X is $CH_2$, Z is CO. The second subset of compounds may be conveniently divided into two groupings as follows:

Group V: 2-[4-(((aryloyl)amino) methyl)phenoxy]-2-methyl propionic acid compounds having the general structural formula illustrated in FIG. 7b.

Group VI: 2-[4-((((aryl)methyl)amino) carbonyl)-phenoxy]-2-methyl<xropionic acid compounds which are the subject matter of the co-pending U.S. patent application Ser. No. 07/623,346 to Abraham et al. filed Dec. 7, 1990.

The $R_{2-9}$ substituents in FIGS. 1b-c are the same as those defined with reference to FIG. 1a. The synthesis of specific chemical compounds within the first five groups of compounds is provided in the following examples with reference to FIGS. 2-7. The synthesis of specific chemical compounds in the sixth group is explained in detail in co-pending U.S. patent application Ser. No. 07/623,346 to Abraham which has been incorporated by reference. All compounds which were prepared were checked by thin layer chromatography (TLC) for purity and the structure elucidation was based on NMR and IR spectroscopy and elemental analysis.

EXAMPLE 1

FIG. 2A illustrates a reaction scheme for preparing 2-(4-aminophenoxy)-2-methyl propionic acid, a compound that is useful as a precursor in the preparation of Group I compounds. In accordance with the scheme of FIG. 2A, 8 grams (g) (0.2 mol) of pulverized sodium hydroxide is added to a suspension of 5.28 g (0.035 mol) of p-acetaminophenol in 23 g (0.4 mol) of acetone. The reaction mixture is stirred at room temperature for ½ hour. Subsequently, 3.58 g (0.03 mol) of chloroform is added dropwise over the course of 30 minutes. The reaction mixture is stirred overnight at room temperature and acetone is removed under vacuum. The residue is dissolved in water (10 ml), followed by acidification with 37% hydrochloric acid (HCl) to produce a pale yellow precipitate of 2-(4-acetaminophenoxy)-2-methyl propionic acid (5 g, 60% yield), crystallized from methanol, mp 69-71° C.

$^1$H NMR: (CD3OD)δ7.1(m,4H) Ar$\underline{H}$, 2.05 (s,3H), C$\underline{H}_3$, 1.45, (s,6H) 2C$\underline{H}_3$ 1.18 g (0.005 mol) of the 2-(4-acetaminophenoxy)-2-methyl propionic acid is boiled in 10% KOH (60 ml) for ½ hour. The solution is then cooled and acidified with acetic acid to yield 0.6 g (62% yield) of 2-(4-aminophenoxy)-2-methyl propionic acid as a yellowish white powder, mp 214-16° C.

$^1$H NMR: (DMSOd6+TMS) δ6.6 (m,4H)Ar$\underline{H}$, 1.35 (s,6H, 2C$\underline{H}_3$)

EXAMPLE 2

FIG. 2B illustrates another reaction scheme for preparing 2-(4-aminophenoxy)-2-methyl propionic acid. In accordance with the scheme of FIG. 2B, 8 grams of potassium hydroxide is dissolved in 32 ml of water and the resultant KOH solution is admixed with 280 ml of 3% hydrogen peroxide. 11.3 g (0.058 mol) of 2-(4-cyanophenoxy)-2-methyl propionic acid is slowly added to the $KOH/H_2O_2$ solution and the reaction mixture is stirred for about one hour until the exotherm and evolution of gas has ceased. The mixture is then cooled and acidified with concentrated hydrochloric acid. The 2-[4-(carboxamido)phenoxy]-2-methyl propionic acid product is obtained as a white solid (9.8 g, 79% yield). The product is crystallized from ethanol to produce pure white crystals, mp 202-4° C.

5.57 g (0.025 mol) of the 2-[4-(carboxamido)phenoxy]-2-methyl propionic acid is added gradually with stirring to 100 ml of an ice cold aqueous solution containing 4.4 g (0.025 mol) of bromine and 11 g (0.25 mol) of sodium hydroxide. The solution thus obtained is warmed at 75° C. for ½ hour. After cooling, the solution is acidified with acetic acid giving the desired 2-(4-aminophenoxy)-2-methyl propionic acid product as 4.0 g (81% yield) of a white precipitate, mp 214-16° C. The compound is identical with the product prepared in Example 1.

EXAMPLE 3

FIG. 2C illustrates a general reaction scheme for preparing the Group I 2-[4-(arylacetamido)phenoxy]-2-methyl propionic acids. In accordance with the illustrated scheme, 1 g (0.005 mol) of 2-(4-aminophenoxy)-2-methyl propionic acid is dissolved with stirring in 10 ml of water containing 0.41 g (0.1 mol) of NaOH. To this solution, 0.79 g (0.005 mol) of phenyl acetyl chloride in 5 ml of tetrahydrofuran (THF) is gradually added over a period of about 15 minutes. After the addition is complete the pH of the reaction mixture should be alkaline (if not a few drops of 2N NaOH is added to assure alkalinity). The reaction mixture is continuously stirred for 1 hour. Thereafter, the THF is evaporated in vacuo, and the solution is then diluted with 5 ml water and acidified with concentrated hydrochloric acid. The product is extracted with ethyl ether (2×20 ml), washed with water (3×20 ml), and then dried over anhydrous $MgSO_4$. Upon addition of petroleum ether to the ether solution, 0.9 g (56% yield) of the 2-[4-(phenylacetamido)phenoxy]-2-methyl propionic acid product precipitates as a pale brown solid, mp 173–175° C.

$^1$H NMR: (DMSOd6) 10 (s,1H, COO$\underline{H}$), 7.5–6.7 (m, 9H, Ar$\underline{H}$), 3.55 (s, 2H, C$\underline{H}_2$), 1.4 (s, 6H, 2C$\underline{H}_3$)
Anal: $C_{18}H_{19}NO_4$
Calculated: C, 69.00, H, 6.07, N, 4.47
Found: C, 68.86, H, 6.14, N, 4.42

EXAMPLE 4

The procedure of Example 3 is followed as above, except that 0.005 mol of 4-chlorophenyl acetyl chloride is substituted for the phenyl acetyl chloride. In this case the product (57% yield) is 2-[4-(p-chlorophenylacetamido)phenoxy]-2-methyl propionic acid, mp 168–71° C.

$^1$H NMR: (DMSOd6) δ 10 (s, 1H, COO$\underline{H}$), 7.6–6.7 (m, 8H, Ar$\underline{H}$), 3.6 (s, 2H, C$\underline{H}_2$), 1.4 (s, 6H, 2C$\underline{H}_3$)
Anal: $C_{18}H_{18}NO_4Cl$
Calculated: C, 62.15, H, 5.17, N, 4.02, Cl 10.12
Found: C, 62.16, H, 5.25, N, 3.98, Cl 10.25

The 4-chlorophenyl acetyl chloride for the foregoing synthesis is prepared by heating to reflux a suspension of 1 g (0.006 mol) of 4-chlorophenyl acetic acid in 1.07 g (0.009 mol) of thionyl chloride with stirring for 1 hour. After cooling, excess thionyl chloride is evaporated under vacuum to present the 4-chlorophenyl acetyl chloride product as a yellow oil (1 g, 83% yield).

EXAMPLE 5

FIG. 3 illustrates a general reaction scheme for preparing the Group II 2-[4-(((aryloxy)carbonyl)amino)-phenoxy]-2-methyl propionic acids. In accordance with the illustrated scheme, a solution consisting of 0.15 g (0.001 mol) of phenyl chloroformate in 3 ml THF is gradually added to an ice cold solution containing 0.3 g (0.001 mol) of 2-(4-amino phenoxy)-2-methyl propionic acid and 0.17 g (0.002 mol) of sodium bicarbonate in 10 ml of water (10 ml). The reaction mixture is stirred for ½ hour at 0° C., followed by stirring for 1 hour at room temperature. The THF is removed in vacuo and 10 ml of water is added. Then, the reaction mixture is acidified with concentrated hydrochloric acid and extracted with ethyl ether (2×20 ml). The ether solution is washed with water (3×20 ml) and dried over anhydrous $MgSO_4$. The desired product, 2-[4-((((phenyl)oxy)carbonyl) amino)phenoxy]-2-methyl propionic acid, is precipitated from the ether solution by addition of petroleum ether as a white solid, 0.15 g (31% yield), mp 183–5° C.

$^1$H NMR: (DMSOd6) δ 10 (s, 1H, COO$\underline{H}$), 7.55–6.75 (m, 9H, Ar$\underline{H}$), 1.4 (s, 6H, 2C$\underline{H}_3$)
Anal: $C_{17}H_{17}O_5N$
Calculated: C, 64.76, H, 5.39, N, 4.44
Found: C, 64.65, H, 5.45, N, 4.43

EXAMPLE 6

The procedure for Example 5 is followed as above except that 0.001 mol of 4-chlorophenyl chloroformate is substituted for the phenyl chloroformate. In this case the 2-[4-((((p-chlorophenyl)oxy)carbonyl)amino)-phenoxy]-2-methyl propionic acid product is obtained as a white precipitate, 0.15 g (28% yield), mp 179–82° C.

$^1$H NMR: (DMSOd6+TMS) δ 7.6–6.8 (m, 8H, Ar$\underline{H}$), 1.4 (s, 6H, 2C$\underline{H}_3$)
Anal: $C_{17}H_{16}O_5NCl$
Calculated: C, 58.36, H, 4.57, Cl, 10.15
Found: C, 58.16, H, 4.68, Cl, 10.35

EXAMPLE 7

FIG. 4 illustrates a general reaction scheme for preparing the Group III compounds of the invention. In accordance with the illustrated scheme, 5.2 g (34 mmol) of 4-hydroxyphenylacetic acid (HPAA) is heated to reflux with an excess of thionyl chloride ($SOCl_2$) for ½ hour. The reaction mixture is then cooled and excess $SOCl_2$ is removed under vacuum. The residue is reacted for 2 hours with 6.3 g (68 mmol) of aniline in 50 ml of refluxing xylene. The reaction mixture is then cooled, washed with dilute HCl, water and brine and extracted with aqueous 2N NaOH. The combined alkali layer is washed with ether, cooled and acidified to provide 7 g of solid N-phenyl-4-hydroxybenzyl amide ($C_{14}H_{12}NO_2$) as an intermediate product (90% yield), mp 138° C. The intermediate product is recrystallized from a 1:2 mixture of acetone and petroleum ether and a 1.13 g (5 mmol) portion is O-alkylated for 12 hours using the procedure of Example 1 with 20 ml acetone, 2.75 g NaOH and 1.25 ml $CHCl_3$. The final pro<xct is 2-[4-((((phenyl)amino)carbonyl) methyl)phenoxy]-2-methyl propionic acid ($C_{18}H_{19}NO_4$), 1.2 g (76% yield), mp 198° C.

EXAMPLE 8

The procedure of Example 7 is repeated using 8.6 g (68 mmol) of 4-chloroaniline rather than the aniline. In this case, the intermediate product is N-(4-chlorophenyl)-4-hydroxy benzylamide ($C_{14}H_{12}ClNO_2$), 7.5 g (84% yield), mp 163° C. 1.3 g of the intermediate product is O-alkylated to produce 2-[4-(((((4-chlorophenyl)amino)carbonyl)methyl) phenoxy]-2-methyl propionic acid ($C_{18}H_{18}ClNO_4$), 0.86 g (50% yield), mp 196° C.

EXAMPLE 9

The procedure of Example 7 is repeated using 2.6 g (17 mmol) of the HPAA and using 5.67 g (35 mmol) of 3,4-dichloroaniline rather than aniline. In this case, the intermediate product is N-(3,4-dichlorophenyl-4-hydroxy benzylamide ($C_{14}H_{11}Cl_2NO_2$). 1.48 g (5 mmol) of the intermediate is O-alkylated to produce 2-[4-(((3,4-dichlorophenyl)amino) carbonyl)methyl)phenoxy]-2-methyl propionic acid ($C_{18}H_{17}Cl_2NO_4$), 0.76 g (40% yield), mp 174° C.

EXAMPLE 10

The procedure of Example 7 is repeated using 2.6 (17 mmol) of the HPAA and using 5.7 g (35 mmol) of 3,5-dichloroaniline rather than aniline. In this case, the intermediate product is N-(3,5-dichlorophenyl-4-hydroxy benzylamide ($C_{14}H_{11}Cl_2NO_2$). 1.48 g (5 mmol) of the intermediate is O-alkylated to produce 2-[4-((((3,5-dichlorophenyl)amino) carbonyl)methyl)- phenoxy]-2-methyl propionic acid ($C_{18}H_{17}Cl_2NO_4$), 0.8 g (42% yield), mp 138° C.

EXAMPLE 11

The procedure of Example 7 is repeated using 0.95 g (6 mmol) <x the HPAA, 2.6 g (12 mmol) of 3,4,5-trichloroaniline rather than aniline, and 25 ml of refluxing xylene. In this case, the intermediate product is N-(3,4,5-trichlorophenyl)-4-hydroxy benzylamide. 0.50 g (1.5 mmol) of the intermediate product is O-alkylated using 10 ml acetone 0.82 g NaOH and 0.37 ml $CHCl_3$ to produce 2-[4-((((3,4,5-trichlorophenyl)amino)carbonyl)methyl)phenoxy]-2-methyl propionic acid ($C_{18}H_{16}Cl_3NO_4$), 0.27 g (43% yield), mp 160° C.

EXAMPLE 12

The procedure of Example 7 is repeated using 5.04 g (32 mmol) of the HPAA, 6 ml (64 mmol) of 4-fluoroaniline rather than aniline, and 25 ml of refluxing xylene. In this case, the intermediate product is N-(4-fluorophenyl)-4-hydroxybenzylamide. 1.22 g (5 mmol) of the intermediate product is O-alkylated to produce 2-[4-((((4-fluorophenyl)amino)carbonyl)methyl)phenoxy]-2-methyl propionic acid ($C_{18}H_{18}FNO_4$), 0.74 g (45% yield), mp 198° C.

EXAMPLE 13

The procedure of Example 7 is repeated using 5.04 (32 mmol) of the HPAA, 8.05 ml (64 mmol) of 4-trifluoromethylaniline rather than aniline, and 25 ml of refluxing xylene. In this case, the intermediate product is N-(4-trifluoromethylphenyl)-4-hydroxy benzylamide. 1.5 g (5 mmol) of the intermediate is used to produce 2-[4-((((4trifluoromethylphenyl)amino)carbonyl)-methyl) phenoxy]-2-methyl propionic acid ($C_{19}H_{18}F_3NO_4$), 0.85 g (44% yield), mp 197° C.

EXAMPLE 14

The procedure of Example 7 is repeated using 5.04 (32 mmol) of the HPAA, 8 g (65 mmol) of 4-methyl aniline rather than aniline, and using 25 ml of refluxing xylene. In this case the intermediate product is N-(4-methylphenyl)-4-hydroxy benzylamide. 1.2 g (5 mmol) of the intermediate is used to produce 2-[4-((((4-methylphenyl)amino)carbonyl)methyl) phenoxy]-2-methyl propionic acid ($C_{19}H_{21}NO_4$), 0.98 g (65% yield), mp 164° C.

EXAMPLE 15

The procedure of Example 7 is repeated using 3.26 (21 mmol) of the HPAA, 5.3 ml (42 mmol) of 3,5-dimethyl aniline rather than aniline, and 25 ml of refluxing xylene. In this case the intermediate product is N-(3,5-dimethylphenyl)-4-hydroxy benzylamide. 1.27 g (5 mmol) of the intermediate is used to produce 2-[4-((((3,5-dimethylphenyl) amino)carbonyl)methyl)-phenoxy]-2-methyl propionic acid ($C_{20}H_{23}NO_4$), 1.15 g (68% yield), mp 85° C. Alternatively, the procedure outlined in the German Patent Application 2,432,560, which is herein incorporated by reference, can be followed to produce the compound of this Example 15.

EXAMPLE 16

The procedure of Example 7 is repeated using 5.04 (32 mmol) of the HPAA, 10 ml (64 mmol) of 4-isopropyl aniline rather than aniline, and using 25 ml of refluxing xylene. In this case the intermediate product is N-(4-isopropylphenyl)-4-hydroxybenzylamide. 1.34 g (5 mmol) of the semi-solid, thick viscous liquid intermediate is used to prepare 2-[4-((((4-isopropylphenyl)amino)carbonyl) methyl)phenoxy]-2-methyl propionic acid ($C_{21}H_{25}NO_4$), 1.1 g (61% yield), mp 141° C.

EXAMPLE 17

With reference to FIGS. 5A, 5B and 5C, a scheme is illustrated for preparing Group IV compounds. In accordance with FIG. 5A, aniline or aniline derivatives may be reacted with phosgene to obtain the carbamoyl chloride. In accordance with FIG. 5B, hydroquinone may be monoacetylated using acetic anhydride. The product is then O-alkylated using acetone, $CHCl_3$ and KOH and then hydrolyzed using a base. The products of the reactions of FIGS. 5A and 5B may then be reacted according to the reaction scheme of Figu<x 5C to produce the Group IV 2-[4-(((arylamino)carbonyl)oxy)phenoxy)]-2-methyl propionic acids.

EXAMPLE 18

As an alternative to the reaction scheme described in Example 7 and shown in FIG. 4, the Group III compounds may be prepared according to the scheme shown in FIG. 6a. 5.2 g (32 mmol) of HPAA, 6.3 g (68 mmol) of aniline, and 25 ml of mesitylene are heated to reflux. 0.74 g (8mmol) of phosphorous pentachloride is added to the refluxing mixture and the reflux is continued for an additional two hours. The reaction mixture is subsequently cooled, washed with dilute HCl, water and brine, and extracted with aqueous 2N sodium hydroxide NaOH. The combined alkali layer is washed with ether, cooled and acidified to provide 7 g (90% yield) of solid N-phenyl 4-hydroxybenzyl amide ($C_{14}H_{12}NO_2$) as an intermediate product, mp 138°. The intermediate product is recrystallized from a 1:2 mixture of acetone:petroleum ether and a 1.13 g (5 mmol) portion is O-alkylated. 1.6 g (30 mmol) of pulverized sodium hydroxide is added to a solution of N-phenyl-4-hydroxybenzamide (1.13g, 5mmol) in 20 ml of acetone. The reaction mixture is stirred overnight at room temperature and acetone is removed under vacuum. The residue is dissolved in 10 ml of water and acidified with 2N HCl to produce a pale yellow solid. The solid is separated, dissolved in methanol, charcoaled, and solvent evaporated to provide 2-[4-((((phenyl)amino)carbonyl)methyl) phenoxy]-2-methyl propionic acid ($C_{18}H_{19}NO_4$), 1.2 g (76% yield), mp 198° C. The last step in the procedure shown in FIG. 6a is the conversion of the acid to the sodium salt via its reaction with sodium bicarbonate. Similar reactions with other salt cations such as potassium and ammonium or reactions to form esters can also be performed.

EXAMPLE 19

Figure 6B:
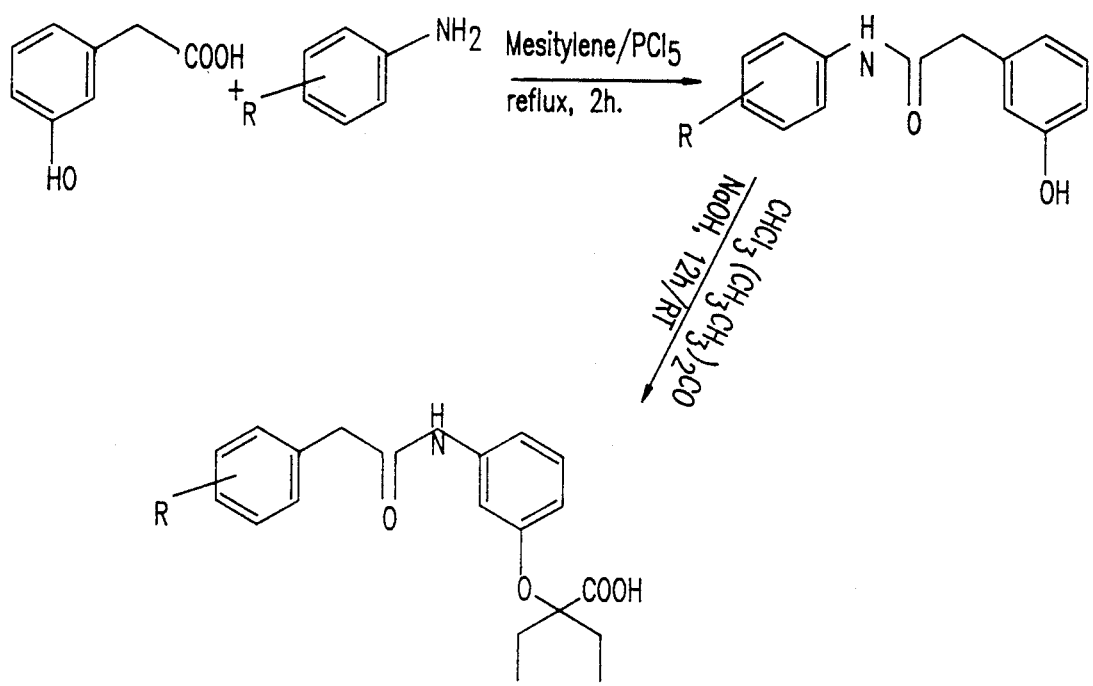
FIG. 6b depicts chemical structures arranged in a reaction scheme similar to that shown in FIG. 6a, except that the precursor compounds utilized are chosen such that the compound produced has a meta-substitution rather than para-substitution on one phenyl ring and so that ethyl rather than methyl groups are present on the substituent moiety of the meta-substituted phenyl ring.

FIG. 6b presents a similar reaction scheme to FIG. 6a, except that 3- rather than 4-hydroxyphenylacetic acid (HPAA) is used as the precursor material so that the final compound has a meta rather than a para substitution. In addition, rather than reacting with acetone (dimethyl ketone) a diethyl ketone is used to position ethyl, rather than methyl, moieties in the group substituted on one of the phenyl rings. By example, 1.5g (10mmol) 3-HPAA and 2.6g (20 mmol) 4-chloroaniline in 20 ml of mesitylene was heated to reflux. Then 0.33g (2.55 mmol) $PCl_5$ solution was then slowly added to the above refluxing solution and the refluxing was continued for two hours. The reaction mixture was then cooled and then worked up as described above to yield 2.2 g (90% yield) of 3-[((4-chloroanilino) carbonyl)methyl]phenol. As described above, chloroform (0.8 ml) was added to a stirred and ice-cooled mixture of 1.23 grams of 3-[((4-chloroanilino)carbonyl)methyl]phenol and 1.6 g NaOH in 15 ml of acetone. The reaction mixture was allowed to warm to room temperature and stirring continued for an additional 10 hours. The usual work-up yielded 2-[3-(((4-chloroanalino)carbonyl) methyl)]phenoxy]-2-methylpropionic acid as a low temperature melting sticky solid (C,H,Cl,N analysis yielded ($C_{18}H_{18}ClNO_4$); NMR $\delta$PPM: 1.42 (6H, s, $CH_3$), 3.61 (2H, s, benzylic $CH_2$), and 6.6–7.75 (8H, m, aromatic H)). However, rather than using acetone as the reaction solvent, diethylketone can be used in the same manner as described above to yield the butanoic acid (as opposed to propanoic acid) structure shown in FIG. 6b.

EXAMPLE 20

With reference to FIGS. 7a, a general reaction scheme for preparing 2-[4-(aminomethyl)phenoxy]-2-methyl propionic acid, a compound that is useful as a precursor to the preparation of the Group V compounds, is presented. In accordance with the illustrated scheme, 2-[4-cyanophenoxy]-2-methyl propionic acid (2 g, 9 mmol), prepared as described in Example 2, and 75 ml of ethanol were placed in a 250 ml Parr hydrogenation bottle. The solution was acidified with concentrated hydrochloric acid (3 ml), then 10% palladium on activated charcoal (0.2 g, 10% wt) was added to the mixture. The reaction mixture was placed on a Parr hydrogenator apparatus at 45 psi of hydrogen pressure and shaken for a period of two hours. The mixture was filtered to remove the catalyst, and the filtrated concentrated under vacuum. Addition of ether precipitated hydrochloride salt of the desired product as white, shiny crystals (2.1 g, 87%).

EXAMPLE 21

FIG. 7B illustrates a general reaction scheme for preparing the Group V compounds used in the present invention. In accordance with the illustration, a solution of benzoyl chloride (0.14g, 1 mmol) in THF (3ml) was added over a 15 minute period to a stirred solution of 2-[4-(aminomethyl)phenoxy]-2-methylpropionic acid (0.24g, 1 mmol) and NaOH (0.08 g, 2 mmol) in 10 ml of water. After the addition of the benzoyl chloride was completed, the reaction mixture was stirred for 1 hour at room temperature. THF was evaporated in vacuo. Acidification of the residue provided the desired compound as an oil which was extracted with ether. The organic layer was washed with water, brine, and aired over anhydrous $MgSO_4$. Subsequent addition of petroleum ether precipitated 2-[4-(benzoylamino)methyl)-phenoxy]-2-methyl propionic acid ($C_{18}H_{19}NO_4$) as a white solid (0.15 g, 48%) mp 176–179° C.

NMR: (DMSO-$d_6$) $\delta$ 1.45 (6H, s, 2$CH_3$), 4.4 (2H, d, $CH_2$), 6.8–7.2 (4H, dd, J=9 Hz, aromatic $\underline{H}$, 7.4–8 (5 H, m, aromatic $\underline{H}$), 9, 1 H, br t, N$\underline{H}$).

EXAMPLE 22

The procedure of Example 21 is repeated using 2-chlorobenzoyl chloride (1 mmol) rather than benzoyl chloride. In this case, the product (58% yield) is 2[4-(((2-chlorobenzoyl)amino)methyl) phenoxy]-2-methyl propionic acid ($C_{18}H_{18}ClNO_4$) mp135–137° C.

EXAMPLE 23

The procedure of Example 21 is repeated, except that 1 mmol of 3-chlorobenzoyl chloride is substituted for benzoyl chloride In this case, the product (53% yield) is 2-[4-(((3-chlorobenzoyl) amino)methyl)phenoxy]-2-methyl propionic acid ($C_{18}H_{18}ClNO_4$) mp 145–146° C.

EXAMPLE 24

The procedure of Example 21 is repeated, except that 1 mmol of 4-chlorobenzoyl chloride is substituted for benzoyl chloride In this case, the product (63% yield) is 2-[4-(((4-chlorobenzoyl) amino)methyl)phenoxy]-2-methyl propionic acid ($C_{18}H_{18}ClNO_4$) mp 186–189° C.

EXAMPLE 25

The procedure of Example 21 is repeated, except that 1 mmol of 3,4-dichlorobenzoyl chloride is substituted for benzoyl chloride In this case, the product (57% yield) is 2-[4-(((3,4-dichlorobenzoyl) amino)methyl)-phenoxy]-2-methyl propionic acid ($C_{18}H_{17}Cl_2NO_4$) mp 186–189° C.

EXAMPLE 26

The procedure of Example 20 is repeated, except that 1 mmol of 3,5-dichlorobenzoyl chloride is substituted for benzoyl chloride. In this case, the product (43% yield) is 2-[4-(((3,5-dichlorobenzoyl) amino)methyl)-phenoxy]-2-methyl propionic acid ($C_{18}H_{17}Cl_2NO_4$) mp 110–113° C.

EXAMPLE 27

The procedure of Example 20 is repeated, except that 1 mmol of 3,4,5-trichlorobenzoyl chloride is substituted for benzoyl chloride. In this case, the product is 2-[4-(((3,4,5-trichlorobenzoyl) amino)methyl)phenoxy]-2-methyl propionic acid ($C_{18}H_{16}Cl_3NO_4$) mp 151–152° C.

Examples 1 through 27 outline the synthesis procedures for producing several compounds within the family of compounds defined by the general structural formula of FIG. 1a. Specifically, Examples 1–19 disclose synthesis procedures for Groups 1–4 compounds within the subset defined by the structural formula of FIG. 1b and Examples 20–27 disclose synthesis procedures for Group 5 compounds within the subset defined by the structural formula of FIG. 1c. The co-pending U.S. patent application Ser. No. 07/623,346 to Abraham et al. filed Dec. 7, 1990, describes the synthesis procedures for Group 6 compounds within the subset defined by the structural formula of FIG. 1c. It should be understood that other compounds within the family of compounds used in the present invention can easily be synthesized by changing the starting materials. All compounds within the family would have a similar mode of binding and would, therefore, all should have the effect of shifting the allosteric equilibrium of hemoglobin towards favoring the low affinity "T" state.

The broad family of compounds contemplated for use in this invention includes compounds defined by the formula:

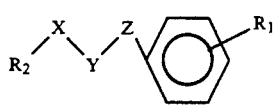

where $R_2$ is a substituted or unsubstituted aromatic such as a phenyl, naphthyl, or indanyl, or heterocyclic aromatic, or a substituted or unsubstituted alkyl ring compound, such as a cyclohexyl or adamantyl, or a substituted or unsubstituted phthalimide compound where X is a carboxyl, Y is a nitrogen and $R_2$ completes the phthalimide compound by being bonded to both X and Y, and where X, Y, and Z are $CH_2$, NH, CO, O or N with the caveat that the X, Y, and Z moieties are each different from one another, and where $R_1$ has the formula:

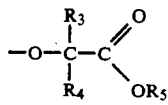

where $R_1$ can be connected to any position on the phenyl ring and $R_3$ and $R_4$ are hydrogen, halogen, methyl, or ethyl groups and these moieties may be the same or different, or alkyl moieties as part of an aliphatic ring connecting $R_3$ and $R_4$, and $R_5$ is a hydrogen, loweralkyl such as methyl, ethyl or propyl, or a salt cation such as sodium, potassium, or ammonium. To this end, compounds have having a naphthyl, adamantyl, or indanyl group at $R_1$ instead of the substituted phenyl like that shown in FIG. 1a have been prepared using substantially the same synthetic routes as described above. In addition, compounds having a phthalimide-like structure have also been synthesized as shown in FIGS. 12a–b and described below in EXAMPLE 28.

EXAMPLE 28

Figure 12A:
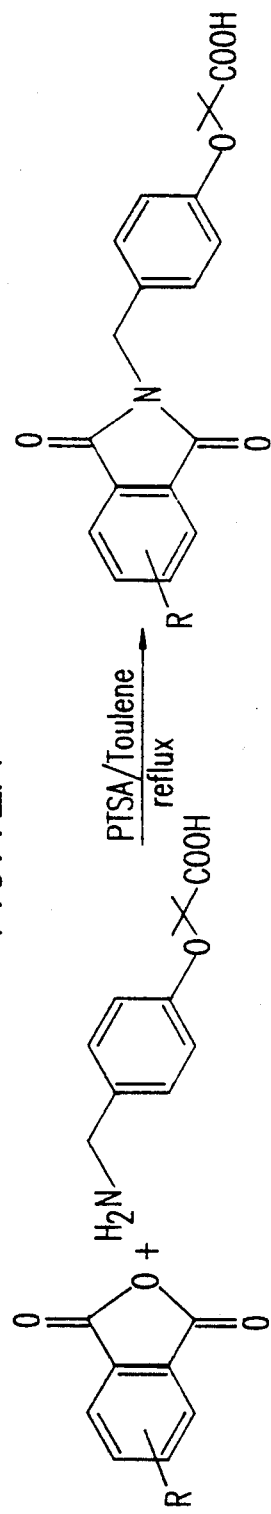
FIG. 12a-b depicts chemical structures in a reaction scheme used to produce a phthalimide form of the compounds within the present invention where the compounds were shown by a measured $P_{50}$ value to allosterically modify hemoglobin towards the low oxygen affinity state.
Figure 12B:
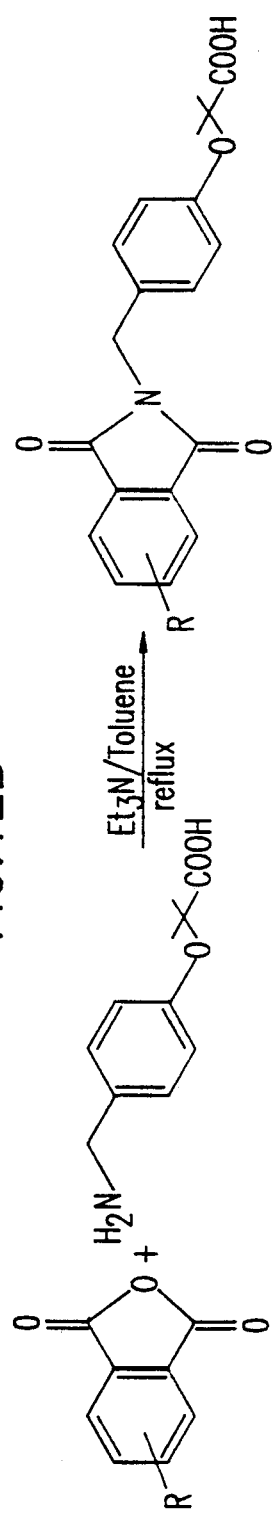

FIGS. 12a and 12b show alternative synthesis routes for preparing 2-[4-((phthalamido)N-methyl)phenoxy)-2-methyl proprionic acid. Phthalic anhydride (0.75g; 5mmol) and 2[4-((amino)methyl)phenoxy]-2-methyl proprionic acid (see FIG. 2B) were refluxed in 25 ml of toluene in the presence of 1 ml triethylamine. Water was removed azeotropically. After four hours of refluxing, the reaction mixture was cooled, toluene was separated, and the above-described work up was provide to yield a crystalline white residue (90% yield; mp 149° C.; NMR δ ppm: 1.46(6H, s, $CH_2$), 4.65(2H, s, $CH_2$), 6.75 and 7.2 (4H, d, J=6Hz, aromatic H of a para substituted ring), and 7.85 (4H, s, aromatic H of a phthalimide unit).

To test the compounds of the invention for physiological activity, human blood was obtained from the Central Blood Bank, Richmond, Va. The extraction, chromatography, and characterization of isolated hemoglobin methods used by the inventors were identical to those described by Dozy and Huisman in *J. of Chromatography*. Vol 32, (1968) pp. 723 and in *The Chromatography of Hemoglobin*, H. J. Schroeder and D. H. J. Huisman, Ed. Marcel Dekker Inc. N.Y. (1980) which are herein incorporated by reference. The purity of normal hemoglobin (HbA) was determined by gel electrophoresis, using a Gelman semimicroelectrophoresis chamber. The concentration of hemoglobin was determined according to the cyanmethemoglobin method described in Zijlstra, *Clin. Chem. Acta.*, Vol 5, pp. 719–726 (1960), and Zijlstra and Van Kamper, *J. Clin. Chem. Clin. Biochem.*, Vol. 19, p. 521 (1981) which are herein incorporate by reference. All purified hemoglobin solutions were stored in liquid nitrogen. The reagents and buffers were purchased from the following sources: Fischer Scientific, Sigma Chemical Company, and Pharmacia and Research Chemicals, Inc.

Oxygen equilibrium curves were determined on an AMINCO ™ HEM-O-SCAN oxygen dissociation analyzer available from Travenol Laboratories. HbA was prepared as follows: 20 ml of whole blood from a nonsmoking donor (blood bank, Richmond, Virginia) was drawn into a heparinized vacutainer. The blood was immediately packed in ice (to prevent MetHb formation) and then centrifuged (10 minutes at 2500 rpm) to separate the plasma and buffy coat from the packed erythrocytes. After centrifugation was completed, the plasma and buffy coat were removed by aspiration and the cells washed three times with 0.9% NaCl containing 40 mg of ethylenediaminetetraacetic acid (EDTA) per liter and then once with 1.0% NaCl containing 40 mg of EDTA/L. The cells were lysed by the addition of one to two volumes of deionized water containing 40 mg of EDTA/L. The mixture was allowed to stand for 30 minutes with occasional mixing before being centrifuged for two hours at 10,000 rpms at 4° C. for two hours to remove the remaining cell stroma. The supernatant was further purified by either gel filtration with Sephadex G-25 or dialysis against pH 8.6 tris buffer (50 mM, containing 40 mg. of EDTA/L). The sodium chloride free hemoglobin solution was chromatographed on DEAE-Sephacel ion-exchange resin (Sigma) preequilibrated with Tris buffer (pH 8.6, 50 mM, containing 40 mg of EDTA/L), the HbA fraction was then eluted with pH 8.4 Tris buffer. The pure HbA fraction (identified by electrophoresis) was concentrated using a Schleicher and Schuell collodion bag apparatus (Schleicher and Schuell, Inc.) with HEPES buffer (150 mM, pH 7.4) as the exchange buffer. The hemoglobin concentration was then determined using the above-noted cyanomethemoglobin method. The hemoglobin concentration at this point was usually found to be around 35g % or approximately 5.5 mM. Less than 5% methemoglobin was noted even after several days at 4° C.

All compounds were mixed with one equivalent of sodium bicarbonate ($NaHCO_3$) (this process converts the carboxylic acid moiety to a sodium salt; see FIG. 6a), then dissolved in the HEPES buffer to give 20 mM solutions. Just prior to running the oxygen equilibrium curve, the hemoglobin and the drug were mixed in a 1:1 ratio (50 μl of hemoglobin plus 50 μl of drug) to give 2.75 mM hemoglobin with- a drug concentration of 10 mM. The control was prepared by the addition of 50 μl of hemoglobin to 50 μl of the HEPES buffer.

Table 1 presents the measured $P_{50}$ value, the $P_{50}$ control value, and the ratio of the measured $P_{50}$ value to the control ($P_{50}/P_{50}C$) for normal hemoglobin treated with several synthesized compounds.

TABLE 1

| COMP. NO. | $R_2$ | $R_3$ | $R_4$ | $R_5$ | $R_6$ | X | Y | Z | $P_{50}$ (CONTROL) | $P_{50}$ | $P_{50}/P_{50}C$ |
|---|---|---|---|---|---|---|---|---|---|---|---|
| 1 | H | H | H | H | H | CO | NH | $CH_2$ | 18 | 35 | 1.94 |
| 2 | CL | H | H | H | H | CO | NH | $CH_2$ | 18 | 27.5 | 1.52 |
| 3 | H | CL | H | H | H | CO | NH | $CH_2$ | 18 | 37.5 | 2.08 |

TABLE 1-continued

| COMP. NO. | $R_2$ | $R_3$ | $R_4$ | $R_5$ | $R_6$ | X | Y | Z | $P_{50}$ (CONTROL) | $P_{50}$ | $P_{50}/P_{50}C$ |
|---|---|---|---|---|---|---|---|---|---|---|---|
| 4 | H | H | CL | H | H | CO | NH | $CH_2$ | 19 | 48 | 2.52 |
| 5 | H | CL | CL | H | H | CO | NH | $CH_2$ | 18 | 40.5 | 2.25 |
| 6 | H | CL | H | CL | H | CO | NH | $CH_2$ | 18 | 47 | 2.60 |
| 7 | H | CL | CL | CL | H | CO | NH | $CH_2$ | 19 | 40 | 2.10 |
| 8 | H | H | H | H | H | $CH_2$ | CO | NH | 19 | 35 | 1.73 |
| 9 | H | CL | H | H | H | $CH_2$ | CO | NH | 18 | 44 | 2.44 |
| 10 | H | H | CL | H | H | $CH_2$ | CO | NH | 19 | 44 | 2.31 |
| 11 | H | H | F | H | H | $CH_2$ | CO | NH | 18 | 35 | 1.94 |
| 12 | H | H | $CH_3$ | H | H | $CH_2$ | CO | NH | 18 | 45 | 2.50 |
| 13 | H | H | $CF_3$ | H | H | $CH_2$ | CO | NH | 18 | 42 | 2.33 |
| 14 | H | H | OME | H | H | $CH_2$ | CO | NH | 18 | 38 | 2.11 |
| 15 | H | CL | CL | H | H | $CH_2$ | CO | NH | 18 | 50 | 2.77 |
| 15 | H | ME | H | ME | H | $CH_2$ | CO | NH | 18 | 52 | 2.88 |
| 16 | H | H | H | H | H | O | CO | NH | 18 | 26.5 | 1.47 |
| 17 | H | H | CL | H | H | O | CO | NH | 19 | 34 | 1.78 |
| 18 | H | H | H | H | H | NH | CO | $CH_2$ | 19 | 54 | 2.84 |
| 19 | H | H | CL | H | H | NH | CO | $CH_2$ | 19 | 54 | 2.84 |
| 20 | H | CL | CL | H | H | NH | CO | $CH_2$ | 18 | 65 | 3.61 |
| 21 | H | CL | H | CL | H | NH | CO | $CH_2$ | 19 | 83 | 4.36 |
| 22 | H | CL | CL | CL | H | NH | CO | $CH_2$ | 19 | 63 | 3.30 |
| 23 | H | H | F | H | H | NH | CO | $CH_2$ | 18 | 45 | 2.50 |
| 24 | H | H | $CF_3$ | H | H | NH | CO | $CH_2$ | 18 | 44 | 2.44 |
| 25 | H | H | $CH_3$ | H | H | NH | CO | $CH_2$ | 18 | 49 | 2.72 |
| 26 | H | $CH_3$ | H | $CH_3$ | H | NH | CO | $CH_2$ | 19 | 75 | 3.94 |
| 27 | CL | H | H | H | CL | NH | CO | $CH_2$ | 18 | 34 | 1.89 |
| 28 | H | ME | ME | H | H | NH | CO | $CH_2$ | 18 | 62 | 3.41 |
| 29 | — | NAPTHYL | | — | — | NH | CO | $CH_2$ | 18 | 58 | 3.20 |
| 30 | H | PROPYL | | H | H | NH | CO | $CH_2$ | 18 | 64 | 3.56 |
| 27 | H | CL | H | H | H | NH | CO | $CH_2$ | 18 | 61 | 3.40 |
| 28 | H | H | CL | H | H | $CH_2$ | NH | CO | 18 | 27 | 1.50 |
| 29 | H | H | $CH_3$ | H | H | $CH_2$ | NH | CO | 19 | 28 | 1.47 |
| 30 | H | CL | CL | H | H | $CH_2$ | NH | CO | 18 | 28 | 1.56 |
| 31 | H | H | H | H | H | $CH_2$ | NH | CO | 19 | 22 | 1.16 |
| 32 | — | INDANYL | | — | — | NH | CO | $CH_2$ | 18 | 64 | 3.56 |
| 33 | — | ADAMANTYL | | — | — | NH | CO | $CH_2$ | 18 | 32 | 1.78 |
| 34 BZF | H | H | CL | H | H | CO | NH | $(CH_2)_2$ | 18 | 33 | 1.83 |

It is noted that the $P_{50}$ control value is less than for normal hemoglobin under physiological conditions (e.g., 26.5) because here the $P_{50}$ was made on hemoglobin in solution (outside the red blood cells). Each hemoglobin sample treated with one of the compounds falling within the family defined by this invention had a $P_{50}$ drug value which was greater than the $P_{50}$ control. This response indicates that the allosteric equilibrium for hemoglobin has been shifted towards favoring the low oxygen affinity "T" state of hemoglobin due to the presence of the compounds. At the bottom of a Table 1 row (34) is presented for bezafibrate (BZF), a known "right-shifting" allosteric hemoglobin modifier. As with all the newly discovered "right-shifting" allosteric hemoglobin modifiers, the hemoglobin treated with BZF had a higher $P_{50}$ than the $P_{50}$ for the control. Table 1 shows the varying $R_{2-6}$ moieties for the substituted phenyl compounds tested, and when a compound which did not have a substituted phenyl, the name of the compound is written across $R_{2-6}$ (e.g., naphthyl, adamantyl, indanyl). The $R_{7-8}$ moieties were methyl groups for each compound tested and the $R_9$ moiety was a sodium cation for each compound tested (derived from the $NaHCO_3$ treatment prior to testing). Because other compounds within the family would have a similar mode of binding (e.g, those with different $R_{2-9}$ moieties), their effect on the $P_{50}$ value can be expected to be the same. The phthalimide structure defined by FIGS. 12a–b and Example 29 had a mean $P_{50}$ value (e.g., $P_{50}$Drug/$P_{50}$Control) of 1.08 indicating the allosteric equilibrium for hemoglobin had been shifted towards favoring the low oxygen affinity "T" state of hemoglobin by the phthalimide compound.

Table 2 shows the effect some of the compounds have on the oxygen dissociation of normal hemoglobin in intact human red blood cells (RBCs).

TABLE 2

| NO. | $R_2$ | $R_3$ | $R_4$ | $R_5$ | $R_6$ | x | z | $P_{50}$ |
|---|---|---|---|---|---|---|---|---|
| CONTROL | — | — | — | — | — | — | — | 27 |
| 21 | H | $CH_3$ | H | $CH_3$ | H | NH | $CH_2$ | 83 |
| 22 | H | Cl | H | Cl | H | NH | $CH_2$ | 87 |
| 23 | H | $CH_3$ | H | $CH_3$ | H | NH | $CH_2$ | 76 |
| 24 | H | $CH_3$ | H | $CH_3$ | H | NH | $CH_2$ | 68 |

The first entry provides the $P_{50}$ value obtained for a of human RBCs alone. The next two entries provide the $P_{50}$ values when the RBCs are mixed together with a 10 millimolar (mM) solution of the sodium salt of either 2-[4-((((3,5-diclorophenyl)amino)carbonyl) methyl)-phenoxy]-2-methyl propionic acid ($C_{18}H_{17}Cl_2NO_4$) (discussed in Example 10) or 2-[4-((((3,5-dimethylphenyl)amino)carbonyl)methyl)phenoxy]-2methyl propionic acid ($C_{20}H_{23}NO_4$) (discussed in Example 15), respectively. Note that the $P_{50}$ values for the hemoglobin in intact RBCs treated with the compounds is much greater than the $P_{50}$ value for untreated hemoglobin under physiological conditions (e.g., the control of 27). In addition, it was determined that the $P_{50}$ value was raised from 27 to 31 in the presence of 1 mM 2-[4((((3,5-dimethylphenyl)amino)carbonyl)methyl)phenoxy]-2-methyl methyl propionic acid and to 42 in the presence of 2 mM 2-[4((((3,5-dimethylphenyl)amino)carbonyl) methyl)phenoxy]-2-methyl propionic acid. This data establishes the permeability of the of the compounds to the cell membrane and that serum albumin does not interfere with the drug's influence on the oxygen dissociation curve of hemoglobin. Entries 23 and 24 in Table 9 provide the $P_{50}$ values for intact RBCs treated with 10 mM of the same two compounds used in entries 21 and 22, respectively, except that the RBCs were washed with a 240 fold excess of 0.9% saline. The relatively slight drop in the $P_{50}$ value after the saline wash, which represents a high retention of allosteric effect, shows that the compounds used in the present invention have high binding affinity for hemoglobin.

Figure 8:
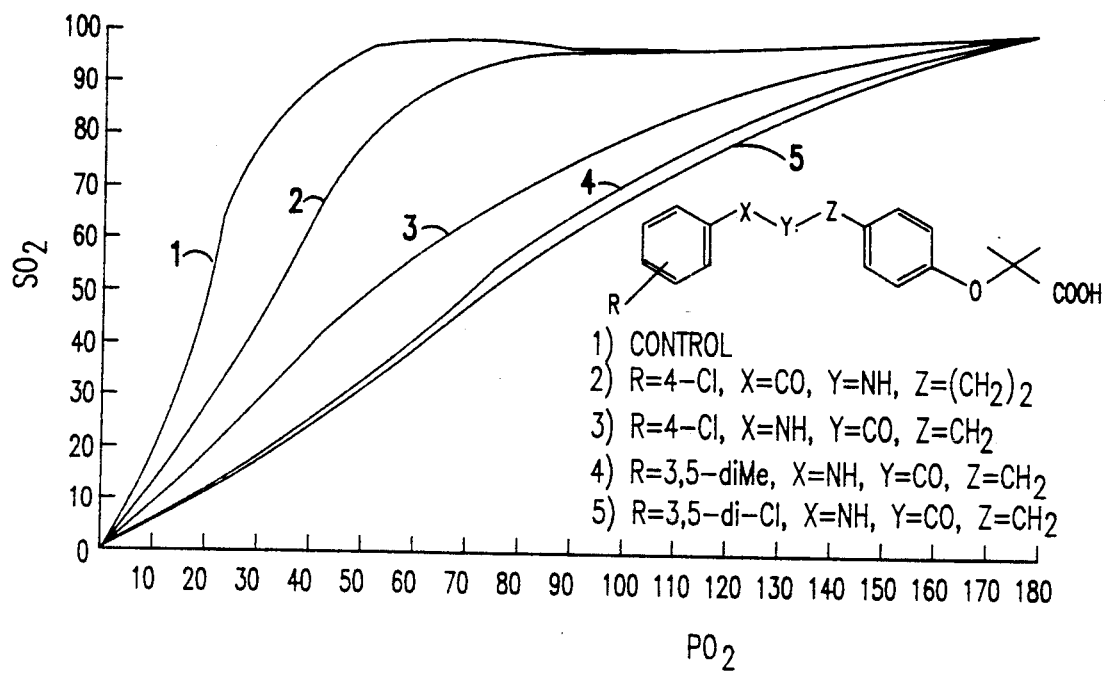
FIG. 8 is a graph illustrating the oxygen dissociation curves produced when a 5.4 millimolar solution of normal hemoglobin in the presence and absence of selected compounds is tested at pH 7.4 using HEPES as the buffer in a Hem-O-Scan oxygen dissociation analyzer.

FIG. 8 is a graph illustrating the oxygen dissociation curves produced when a 5.4 millimolar solution of normal hemoglobin is tested at pH 7.4 using HEPES as the buffer in a Hem-O-Scan oxygen dissociation analyzer. As described above, the $P_{50}$ values reported in Table 1 were determined from curves like those shown in FIG. 8. With particular reference to FIG. 8, the percent oxygen saturation ($SO_2$ on the vertical axis) is plotted against the partial pressure of oxygen ($PO_2$ on the horizontal axis). Curve number 1 shows the oxygen dissociation curve (ODC) in the absence of an allosteric modifying agent. Curve number 2 shows the ODC has been shifted to the right when 10 mM bezafibrate (a known right shifting agent) solubilized with an equimolar amount of $NaHCO_3$ is added to the hemoglobin. It should be noted that as the curve is right shifted to a lower oxygen affinity state, the $P_{50}$ value increases. Curve number 3 shows the right shift caused by adding a 10 mM concentration of 2-[4-((((4-chlorophenyl) amino)carbonyl)methyl)phenoxy]-2-methyl propionic acid ($C_{18}C_{18}ClNO_4$) (described in Example 8 above) to the hemoglobin. Curve number 4 shows the right shift caused by adding a 10 mM concentration of 2-[4-((((3,5-dimethylphenyl)amino)carbonyl)methyl) phenoxy]-2-methyl propionic acid ($C_{20}H_{23}NO_4$) (described in Example 15) to the hemoglobin. Finally, curve number 5 shows the right shift caused by adding a 10 mM concentration of 2-[4-((((3,5-dichlorophenyl)amino)carbonyl)methyl)phenoxy]-2-methyl propionic acid ($C_{18}H_{17}Cl_2NO_4$) (described in Example 10) to the hemoglobin. The right shifting effect shown in FIG. 8 indicates the compounds may be used to lower the oxygen affinity of hemoglobin.

Figure 9:
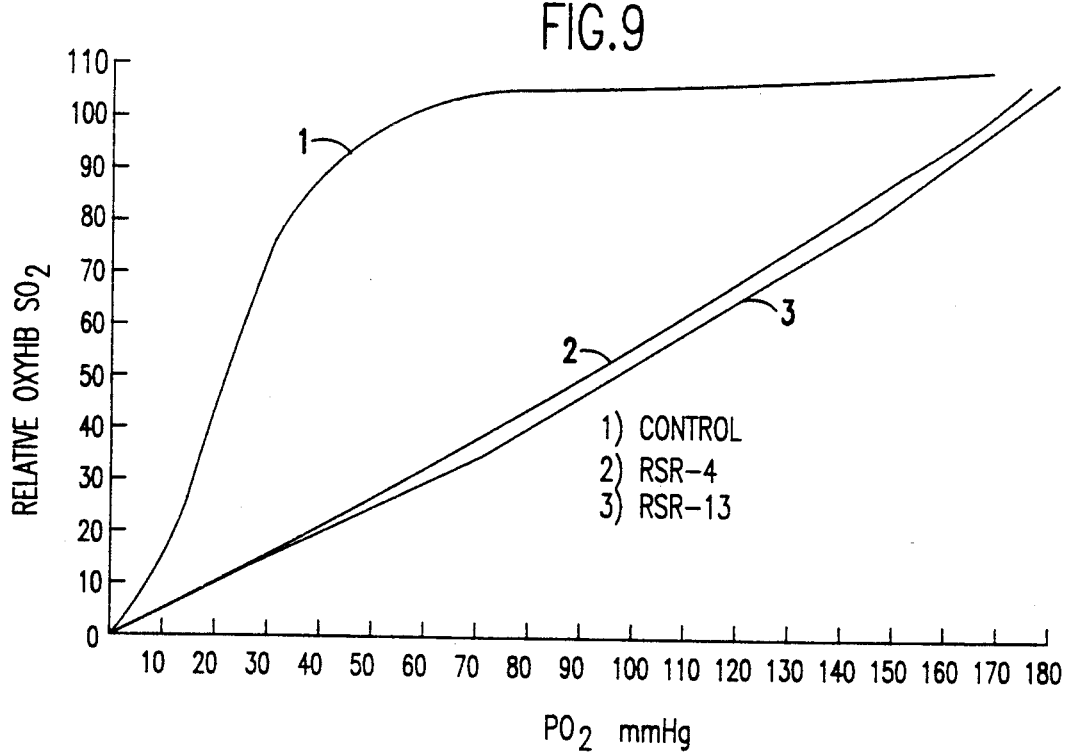
FIG. 9 is a graph similar to FIG. 8 which illustrates oxygen dissociation curves for whole human blood in the presence and absence of selected compounds.

FIG. 9 illustrates the effect of particular compounds on the ODC of whole human blood. Like FIG. 8, the percent oxygen saturation is plotted against the partial pressure of oxygen. As described above, the $P_{50}$ values reported in Table 2 were determined from curves like those shown in FIG. 9. For these curves. 50μl of whole human blood was mixed with a 50 μl solution of the test compound in HEPES buffer at pH 7.4. Curve number 1 shows the ODC of hemoglobin in unreacted whole blood. Curves 2 and 3 respectively illustrate the right shifting effect of the salts of a 10 mM concentration of 2-[4-((((3,5-dimethylphenyl amino)carbonyl)methyl)phenoxy]-2-methyl propionic acid ($C_{20}H_{23}NO_4$) (described in Example 15) or a 10 mM concentration of 2-[4-((((3,5-dichlorophenyl)amino) carbonyl)methyl)phenoxy]-2-methyl propionic acid ($C_{18}H_{17}Cl_2NO_4$) (described in Example 10) on hemoglobin in whole blood.

Figure 10:
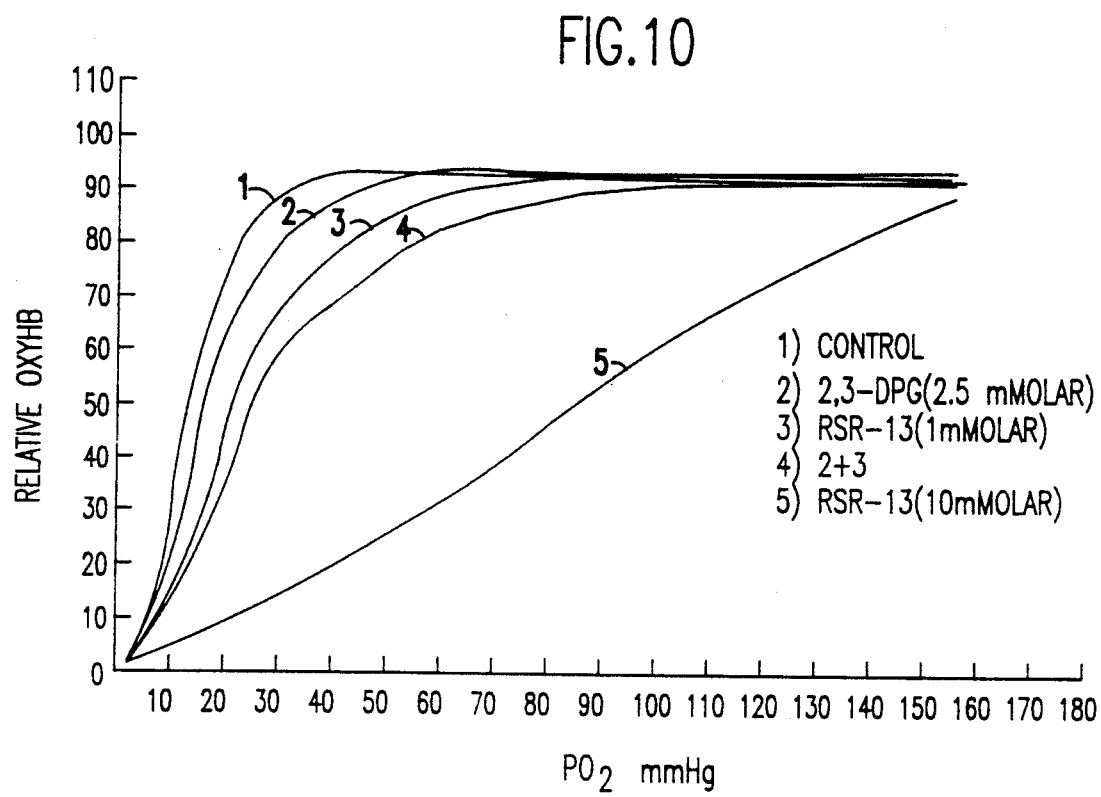
FIG. 10 is a graph similar to FIG. 8 where the oxygen dissociation curves produced are for a 5.4 millimolar solution of normal hemoglobin in the presence and absence of particular compounds, including 2,3-diphosphoglycerate which is the natural allosteric hemoglobin effector, are tested at pH 7.4 using HEPES as the buffer in a Hem-O-Scan oxygen dissociation analyzer.

FIG. 10 shows ODC curves of human hemoglobin (5.4mM) in HEPES buffer at ph 7.4 which were made in a manner similar, to that described in conjunction with FIG. 8. Like FIGS. 8 and 9, the percent oxygen saturation is plotted against the partial pressure of oxygen. Curve number 1 shows ODC of human hemoglobin in the absence of any allosteric modifying agent. Curves 2 and 3 show the right shifting effect of 1 mM and 10 mM concentrations of 2-[4-((((3,5-dimethylphenyl)amino)carbonyl)methyl) phenoxy]-2-methyl propionic acid ($C_{20}H_{23}NO_4$) (described in Example 15) on human hemoglobin. Hence, this compound forces hemoglobin to a lower oxygen affinity state. Curve number 4 shows the right shifting effect of 2.5 mM 2,3-diphosphoglycerate (2,3-DPG) which is a natural allosteric hemoglobin effector. Curve number 5 shows the combined effect of two effectors, e.g., 1 mM 2-[4-((((3,5-dimethylphenyl)amino)carbonyl) methyl)-phenoxy]-2-methyl propionic acid and 2.5 mM 2,3-DPG, is greater than either effector alone. The synergistic effect may be utilized such that smaller quantities of drug are added to blood.

Table 3 illustrates the utility of 2-[4-((((3,5-dimethylphenyl)amino)carbonyl)methyl) phenoxy]-2-methyl propionic acid (called RSR-13) in preserving the oxygen affinity of hemoglobin in stored blood.

TABLE 3

| PACKED RBC | $P_{50}$ IN PRESENCE OF RSR-13 | | |
|---|---|---|---|
| DAY OLD | 0 mM | 1 mM | 2 mM |
| FRESH | 38 | — | — |
| 40 | 32 | 39 | 45 |
| 50 | 33 | 39 | 45 |
| 60 | 34 | 40 | 47 |
| 70 | 35 | 39 | 50 |

RSR-13, 1 mM and 2 mM, was added to samples of human RBCs (packed cells) which were stored at 4° C. in standard adsol formulation 40–70 days. As can be seen from Table 3, the ODC of untreated blood leftshifts overtime (indicated by a drop in the $P_{50}$ value) to a high oxygen affinity state. The increase in oxygen affinity of stored blood is attributed to a decreased concentration of 2,3-DPG. The $P_{50}$ value of 40 day old untreated samples left shifted to 32; however, samples treated with 1 mM RSR-13 remained relatively unchanged ($P_{50}$=90) and those treated with 2 mM RSR-13 were right shifted ($P_{50}$=45). FIG. 13 shows similar concentration dependent effects Lf RSR-13 on the ODCs of 50, 60, 70 day old packed cells. Because of the glycolytic metabolism, the pH of untreated red cells dropped over a period of time from 6.85 at 40 days to 6.6 for 70 day old samples and this would possibly explain the slight right shifting of untreated 70 day old samples compared to 40 day old samples under the Bohr effect. The pH of red blood cells treated with RSR-13 was consistently lower than untreated samples, which suggests that RSR-13 favorably decreases the rate of glycolytic metabolism. RSR-13 had no adverse effect on the stability of RBCs as evidenced by consistent RBC counts in treated and untreated samples. Similarly, the amount of hemolysis was consistent in both treated and untreated sample of packed cells.

Figure 11:
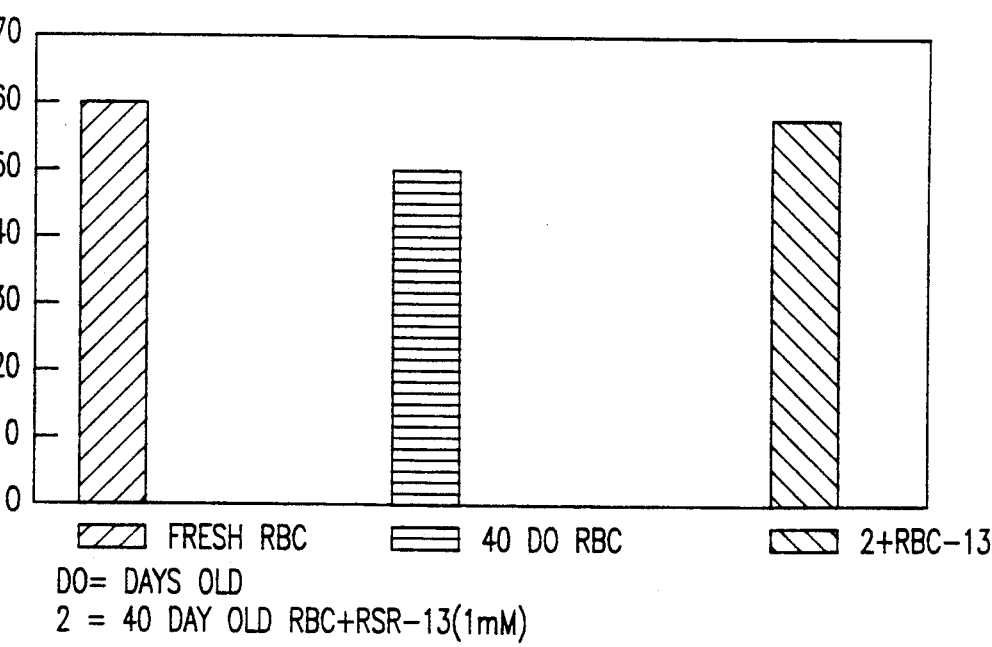
FIG. 11 is a bar graph showing the percentage oxygen delivered by packed cells, fresh stored and in the presence of 2-[4-((((3,5-dimethylphenyl) amino)carbonyl)methyl)phenoxy]-2-methyl propionic acid ($C_{20}H_{23}NO_4$), respectively.

FIG. 11 shows the percentage oxygen delivered, ΔY, by packed cells. Changes in the oxygen saturation ΔY was calculated by Hill's equation (discussed in Stryer, Biochemistry, W. H. Freeman and Co., San Francisco, 1975, Chapter 4, pp, 71–94, which are herein incorporated by reference) at 100 to 30 torr. Column 1 shows the ΔY (59) corresponding to the untreated packed red blood cells. Column 2 shows the ΔY (50) of packed red blood cells stored for 40 days at 4° C. in the best available adsol formulation. Column 3 shows that the ΔY=58 for 40 day old packed cells treated with RSR-13 (1 mM), which is comparable to fresh packed cells. Note, that the decrease (approximately 10%) in the oxygen delivery by packed cells is corrected by the addition of 1 mmol RSR-13.

Table 4 shows the change in the $P_{50}$ values of outdated packed red blood cells on treatment with 2-[4-((((3,5-dimethylphenyl)amino)carbonyl)methyl), phenoxy]-2-methyl propionic acid (RSR-13).

TABLE 4

| PACKED RBC DAY OLD | $P_{50}$ UPON ADDITION OF RSR-13 | | |
|---|---|---|---|
| | 0 mM | 1 mM | 2 mM |
| FRESH | 38 | — | — |
| 40 | 32 | 38 | 42 |
| 50 | 31 | 38 | 45 |
| 60 | 34 | 39 | 46 |

50 μl of 40, 50, and 60 day old red cells were 50 μl of RSR-13 to give final concentrations of RSR-13 at 1 mmol and 2 mmol. Control samples were prepared by mixing 1:1 packed cells and buffer. As can be seen from Table 4, the $P_{50}$ value of untreated samples were consistently lower than samples treated with RSR-13. In addition, a comparison of the results for the fresh red cells with red cells which were aged 40, 50, and 60 days shows a sharp decline in $P_{50}$ value with age. The $P_{50}$ values of 40, 50, 60 day old red cell samples treated with 1 mmol RSR-13 were comparable to the $P_{50}=38$ value found for fresh red cells. These results show that the addition of RSR-13 to the stored red cells restores the cells oxygen affinity.

Since the compounds contemplated by this invention are capable of allosterically modifying hemoglobin so that a low oxygen affinity "T" state is favored (right shifting the equilibrium curve as indicated by the $P_{50}$ column in Tables 1-2 these compounds will be useful in a variety of disease states in mammals including humans where tissues suffer from low oxygenation, such as cancer and ischemia. As pointed out by Hirst et al. in Radiat. Res., Vol. 112, (i , pp. 164, decreasing the oxygen affinity of hemoglobin in circulating blood has been shown to be beneficial in the radiotherapy of tumors. The compounds may be administered to patients in whom the affinity of hemoglobin for oxygen is abnormally high. Particular conditions include certain hemoglobinopathies and certain respiratory distress syndromes in new born infants aggravated by high fetal hemoglobin levels and when the availability of hemoglobin/oxygen to the tissues is decreased (e.g., in ischemic conditions such as peripheral vascular disease, coronary occlusion, cerebral vascular accidents, or tissue transplant). The compounds may also be used to inhibit platelet aggregation and may be used for antithrombotic purposes and wound healing. Topical application could be used for wound healing. In addition, the compounds may be used to treat low oxygen related disorders in the brain such as Alzheimer's disease, depression, and schizophrenia. It may be desirable to administer the compounds to a patient prior to and/or simultaneously with the transfusion of the treated whole blood or red blood cells in order to avoid substantial variations in the hemoglobin oxygen affinity due to dilution that occurs when the blood is administered.

The compounds can be added to whole blood or packed cells preferably at the time of storage or at the time of transfusion in order to facilitate the dissociation of oxygen from hemoglobin and improve the oxygen delivering capability of the blood. Preferably, the compounds would be added in an amount of about 50 mg to 1 g per unit of blood (473 ml) or unit of packed cells (235 ml). When blood is stored, the hemoglobin in the blood tends to increase its affinity for oxygen by losing 2,3-diphosphoglycerides. As described above, the compounds of this invention are capable of reversing and/or preventing the functional abnormality of hemoglobin which is observed when whole blood or packed cells are stored. The compounds may be added to whole blood or red blood cell fractions in a closed system using an appropriate reservoir in which the compound is placed prior to storage or which is present in the anticoagulating solution in the blood collecting bag.

Administration can be achieved orally, by intravenous or intraperitoneal injection, or rectally by suppository where the dose and the dosing regiment is varied according to individual sensitivity and the type of disease state being treated. Studies with mice have shown that a mg/kg/day dose of 2-[4((((3,5-dimethylphenyl)amino)carbonyl)methyl)phenoxy]-2-methyl propionic acid ($C_{20}H_{23}NO_4$) (discussed in Example 15) given intraperitoneally is well tolerated. If the compounds are used for wound healing, the compounds could advantageously be applied topically directly to the wound area. In addition the compounds can be mixed with blood external to a patient's body prior to and/or simultaneously with a transfusion. The compounds can be administered in the pure form or in a pharmaceutically acceptable formulation including suitable elixirs, binders, and the like or as pharmaceutically acceptable salts or other derivatives. It should be understood that the pharmaceutically acceptable formulations and salts include liquid and solid materials conventionally utilized to prepare injectable dosage forms and solid dosage forms such as tablets and capsules. Water may be used for the preparation of injectable compositions which may also include conventional buffers and agents to render the injectable composition isotonic. Solid diluents and excipients include lactose starch, conventional disintegrating agents, coatings and the like.

While the invention has been described in terms of its preferred embodiments, those skilled in the art will recognize that the invention can be practiced with modification within the spirit and scope of the appended claims.

Having thus described our invention, what we claim as new and desire to secure by Letters Patent is as follows:

1. A method for allosterically modifying hemoglobin comprising the step of exposing hemoglobin to a compound of the general structural formula:

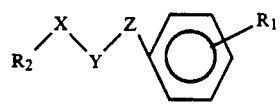

where $R_2$ is a substituted or unsubstituted aromatic compound, or a substituted or unsubstituted alkyl ring compound, or a substituted or unsubstituted phthalimide compound where X is a carboxyl, Y is a nitrogen and $R_2$ completes the phthalimide compound by being bonded to both X and Y, and where X, Y, and Z are $CH_2$, NH, CO, O or N with the caveat that the X, Y, and Z moieties are each different from one another, and where $R_1$ has the formula[.

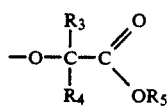

where $R_1$ can be connected to any position on the phenyl ring, and where $R_3$ and $R_4$ are hydrogen, halogen, methyl, or ethyl groups and these moieties may be the same or different, or alkyl moieties as part of an aliphatic ring connecting $R_3$ and $R_4$, and where $R_5$ is a hydrogen, halogen, $C_{1-3}$ loweralkyl, or a salt cation.

2. A method for allosterically modifying hemoglobin comprising the step of exposing hemoglobin to a compound of the general structural formula:

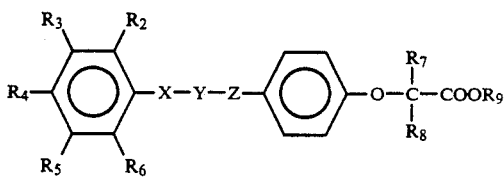

wherein X, Y and Z may each be $CH_2$, CO, NH or O, with the caveat that the X, Y and Z moieties are each different from one another, and wherein $R_{2-6}$ are either hydrogen, halogen, or a substituted or unsubstituted $C_{1-3}$ alkyl group, or a $C_{1-3}$ ether or ester, and these moieties may be the same or different, or alkyl moieties of an aromatic or aliphatic ring incorporating two of the $R_{2-6}$ sites, and wherein $R_{7-8}$ are hydrogen, methyl or ethyl groups and these moieties may be the same or different, or alkyl moieties as part of an aliphatic ring connecting $R_7$ and $R_8$, and wherein $R_9$ is a hydrogen, halogen, substituted or unsubstituted $C_{1-3}$ loweralkyl, or a salt cation.

3. A method for treating blood such that hemoglobin in said blood is allosterically modified towards a low oxygen affinity state, comprising the step of exposing said blood to a compound of the general structural formula:

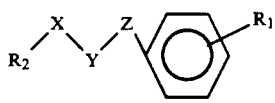

where $R_2$ is a substituted or unsubstituted aromatic compound, or a substituted or unsubstituted alkyl ring compound, or a substituted or unsubstituted phthalimide compound where X is a carboxyl, Y is a nitrogen and $R_2$ completes the phthalimide compound by being bonded to both X and Y, and where X, Y, and Z are $CH_2$, NH, CO, O or N with the caveat that the X, Y, and Z moieties are each different from one another.

and where $R_1$ has the formula:

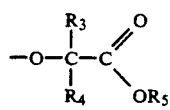

where $R_1$ can be connected to any position on the phenyl ring, and where $R_3$ and $R_4$ are hydrogen, halogen, methyl, or ethyl groups and these moieties may be the same or different, or alkyl moieties as part of an aliphatic ring connecting $R_3$ and $R_4$, and where $R_5$ is a hydrogen, halogen, $C_{1-3}$ loweralkyl, or a salt cation.

4. A method for treating blood such that hemoglobin in said blood is allosterically modified towards a low oxygen affinity state, comprising the step of exposing said blood to a compound of the general structural formula:

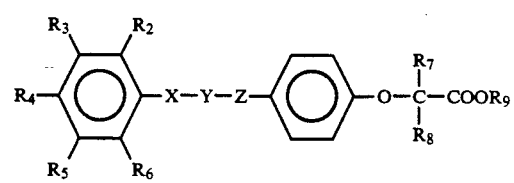

wherein X, Y and Z may each be $CH_2$, CO, NH or O, with the caveat that the X, Y, and Z moieties are each different from one another, and wherein $R_{2-6}$ are either hydrogen, halogen, or a substituted or unsubstituted $C_{1-3}$ alkyl group, or a $C_{1-3}$ ether or ester, and these moieties may be the same or different, or alkyl moieties of an aromatic or aliphatic ring incorporating two of the $R_{2-6}$ sites, and wherein $R_{7-8}$ are hydrogen, methyl or ethyl groups and these moieties may be the same or different, or alkyl moieties as part of an aliphatic ring connecting $R_7$ and $R_8$, and wherein $R_9$ is a hydrogen, halogen, substituted or unsubstituted $C_{1-3}$ loweralkyl, or a salt cation.

5. A method of storing blood, comprising the steps of exposing blood to be stored to a compound of the general structure formula:

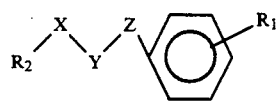

where $R_2$ is a substituted or unsubstituted aromatic compound, or a substituted or unsubstituted alkyl ring compound, or a substituted or unsubstituted phthalimide compound where X is a carboxyl, Y is a nitrogen and $R_2$ completes the phthalimide compound by being bonded to both X and Y, and where X, Y, and Z are $CH_2$, NH, CO, O or N with the caveat that the X, Y, and Z moieties are each different from one another, and where $R_1$ has the formula:

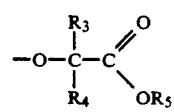

where $R_1$ can be connected -o any position on the phenyl ring, and where $R_3$ and $R_4$ are hydrogen, halogen, methyl, or ethyl groups and these moieties may be the same or different, or alkyl moieties as part of an aliphatic ring connecting $R_3$ and $R_4$, and where $R_5$ is a hydrogen halogen, $C_{1-3}$ loweralkyl, or a salt cation.

6. A method of storing blood, comprising the steps of exposing blood to be stored to a compound of the general structural formula:

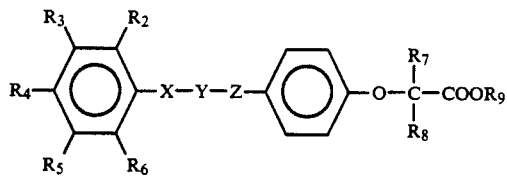

wherein X, Y and Z may each be $CH_2$, CO, NH or O, with the caveat that the X, Y, and Z moieties are each different from one another, and wherein $R_{2-6}$ are either hydrogen, halogen, or a substituted or unsubstituted $C_{1-3}$ alkyl group, or a $C_{1-3}$ ether or ester, and these moieties may be the same or different, or alkyl moieties of an aromatic or aliphatic ring incorporating two of the $R_{2-6}$ sites, and wherein $R_{7-8}$ are hydrogen, methyl or ethyl groups and these moieties may be the same or different, or alkyl moieties as part of an aliphatic ring connecting $R_7$ and $R_8$, and wherein $R_9$ is a hydrogen, halogen, substituted or unsubstituted $C_{1-3}$ loweralkyl, or a salt cation.

7. A method of restoring the oxygen affinity of red blood cells, comprising the steps of storing red blood cells for a period of time; and exposing said red blood cells to a compound of the general structure formula:

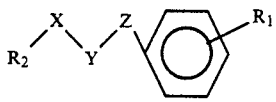

where $R_2$ is a substituted or unsubstituted aromatic compound, or a substituted or unsubstituted alkyl ring compound, or a substituted or unsubstituted phthalimide compound where X is a carboxyl, Y is a nitrogen and $R_2$ completes the phthalimide compound by being bonded to both X and Y, and where X, Y, and Z are $CH_2$, NH, CO, O or N with the caveat that the X Y, and Z moieties are each different from one another, and where $R_1$ has the formula:

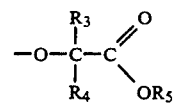

where $R_1$ can be connected to any position on the phenyl ring, and where $R_3$ and $R_4$ are hydrogen, halogen, methyl, or ethyl groups and these moieties may be the same or different, or alkyl moieties as part of an aliphatic ring connecting $R_3$ and $R_4$, and where $R_5$ is a hydrogen, halogen, $C_{1-3}$ loweralkyl, or a salt cation.

8. A method of restoring the oxygen affinity of red blood cells, comprising the steps of storing red blood cells for a period of time; and exposing said red blood cells to a compound of the general structural formula:

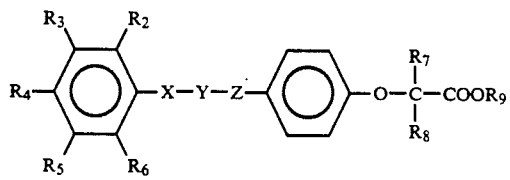

wherein X, Y and Z may each be $CH_2$, CO, NH or O, with the caveat that the X, Y, and Z moieties are each different from one another, and wherein $R_{2-6}$ are either hydrogen, halogen, or a substituted or unsubstituted $C_{1-3}$ alkyl group, or a $C_{1-3}$ ether or ester, and these moieties may be the same or different, or alkyl moieties of an aromatic or aliphatic ring incorporating two of the $R_{2-6}$ sites, and wherein $R_{7-8}$ are hydrogen, methyl or ethyl groups and these moieties may be the same or different, or alkyl moieties as part of an aliphatic ring connecting $R_7$ and $R_8$, and wherein $R_9$ is a hydrogen, halogen, substituted or unsubstituted $C_{1-3}$ loweralkyl, or a salt cation.

* * * * *